US012708420B2

(12) United States Patent
Shiner et al.

(10) Patent No.: US 12,708,420 B2
(45) Date of Patent: Aug. 18, 2026

(54) CERCLAGE CABLE SYSTEM AND APPARATUS

(71) Applicant: GLOBUS MEDICAL, INC., Audubon, PA (US)

(72) Inventors: Zachary C. Shiner, Philadelphia, PA (US); David Machamer, Glen Mills, PA (US); Spiro Kokolis, Norristown, PA (US)

(73) Assignee: Globus Medical, Inc., Audubon, PA (US)

( * ) Notice: Subject to any disclaimer, the term of this patent is extended or adjusted under 35 U.S.C. 154(b) by 275 days.

(21) Appl. No.: 18/469,898

(22) Filed: Sep. 19, 2023

(65) Prior Publication Data

US 2024/0041509 A1 Feb. 8, 2024

Related U.S. Application Data

(62) Division of application No. 17/150,273, filed on Jan. 15, 2021, now Pat. No. 11,813,011.

(51) Int. Cl.

| | |
|---|---|
| ***A61B 17/88*** | (2006.01) |
| ***A61B 17/82*** | (2006.01) |
| *A61B 17/00* | (2006.01) |
| *A61B 17/56* | (2006.01) |
| *A61B 17/80* | (2006.01) |
| *A61B 90/00* | (2016.01) |

(52) U.S. Cl.

CPC .......... *A61B 17/8869* (2013.01); *A61B 17/82* (2013.01); *A61B 2017/00477* (2013.01); *A61B 2017/564* (2013.01); *A61B 17/8019* (2013.01); *A61B 17/8863* (2013.01); *A61B 2090/064* (2016.02)

(58) Field of Classification Search

CPC . A61B 17/8869; A61B 17/82; A61B 17/8019; A61B 17/8863; A61B 2017/00477; A61B 2017/564; A61B 2090/064

See application file for complete search history.

(56) References Cited

U.S. PATENT DOCUMENTS

| | | | |
|---|---|---|---|
| 7,645,282 | B2 | 1/2010 | Huxel et al. |
| 8,343,155 | B2 | 1/2013 | Fisher et al. |
| 9,439,698 | B2 | 9/2016 | Songer et al. |
| 9,707,025 | B2 | 7/2017 | Cavallazzi |
| 10,201,376 | B2 | 2/2019 | Cavallazzi et al. |
| 2005/0144884 | A1 | 7/2005 | Moriya |

(Continued)

*Primary Examiner* — Sameh R Boles

(57) ABSTRACT

A cerclage cable system is disclosed which includes a bone plate, one or more securing devices, and one or more cerclage cables. The bone plate includes a plurality of bone plate apertures thereupon, wherein the bone plate is configured to be affixed to a bone. The one or more securing devices include a body having a proximal end and a distal end, wherein at least one securing device aperture is disposed toward the proximal end, wherein the distal end of the securing device is configured to be inserted into and received by the plurality of bone plate apertures. The one or more cerclage cables include two terminal ends, wherein the one or more cerclage cables are wrapped around the bone, wherein one terminal end of the one or more cerclage cables is passed through at least one securing device aperture.

14 Claims, 24 Drawing Sheets

(56) References Cited

U.S. PATENT DOCUMENTS

| | | | | |
|---|---|---|---|---|
| 2010/0042106 | A1 * | 2/2010 | Bryant ............... | A61B 17/8869 606/103 |
| 2014/0249530 | A1 | 9/2014 | Babikian et al. | |
| 2017/0202589 | A1 | 7/2017 | Dell'oca | |
| 2018/0161083 | A1 | 6/2018 | Kobayashi | |
| 2019/0350578 | A1 | 11/2019 | Petry et al. | |

* cited by examiner

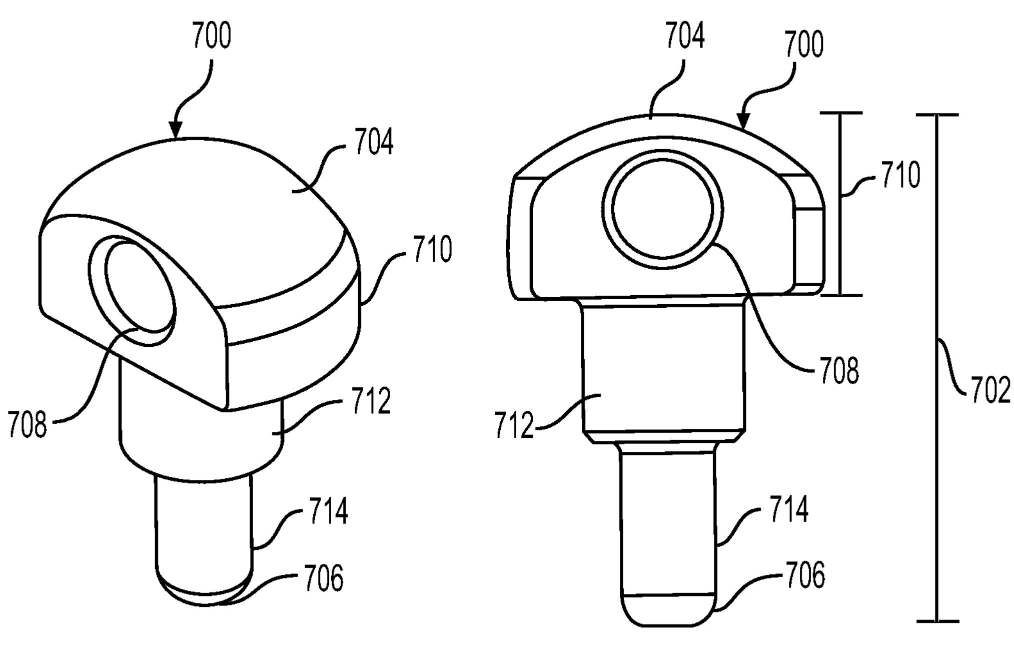
FIG. 7A
FIG. 7B
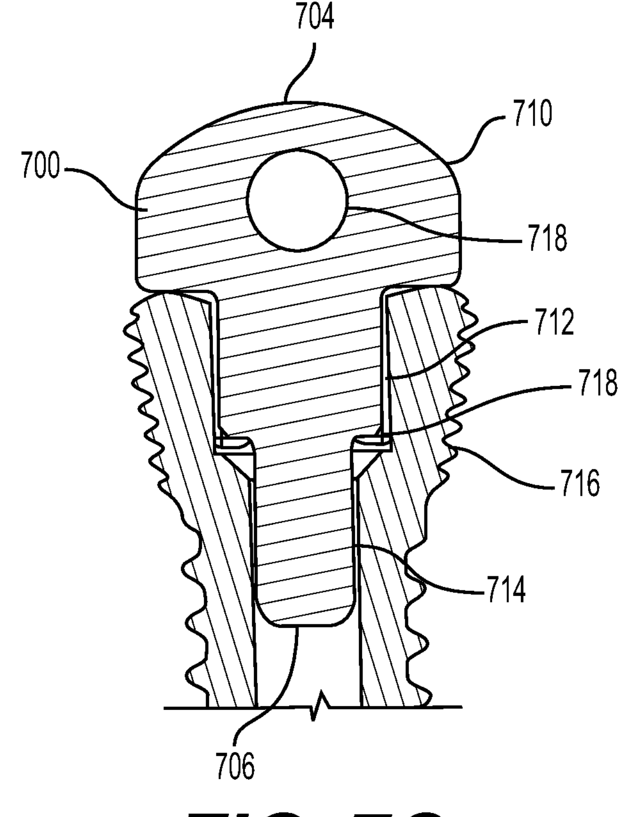
FIG. 7C

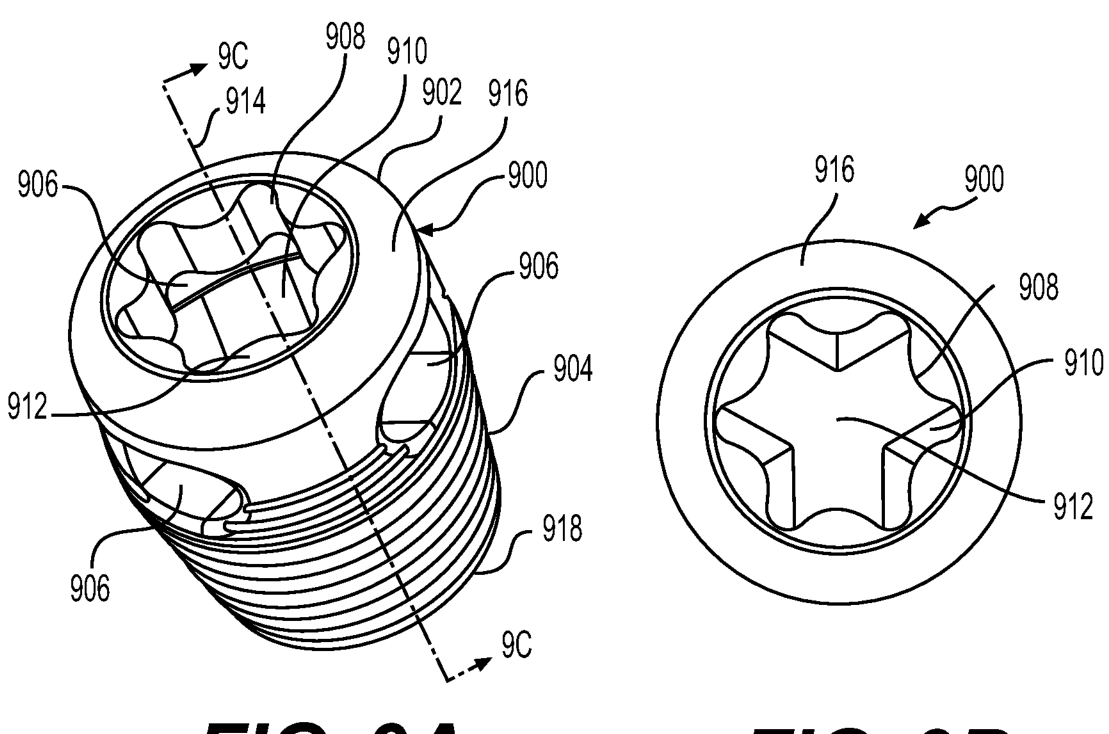
FIG. 9A
FIG. 9B
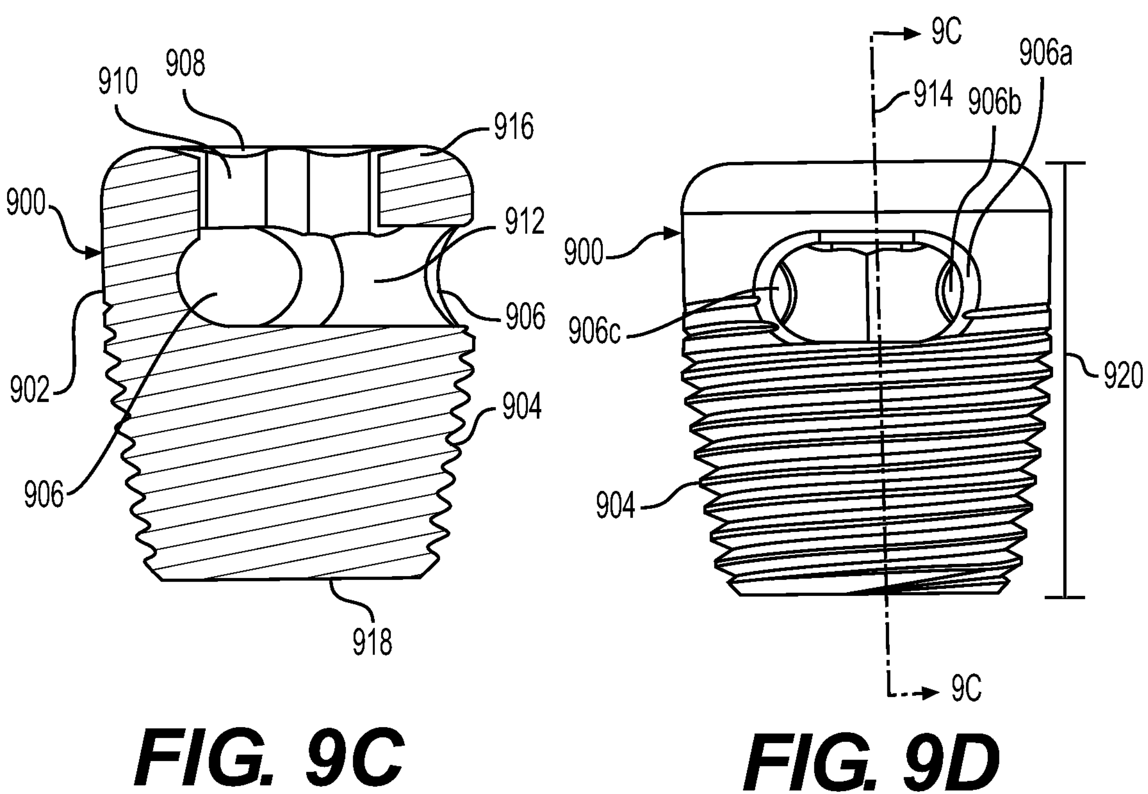
FIG. 9C
FIG. 9D 1206
1216
1218
1214
1210
1200
1208
1212
1204
1202

1206
1216
1218
1214
1210
1200
1208
1212
1204
1202

1200
1208
1214
1210
1206
1216
1218
1204
1212
1202

1312
b
1304
1326
104
a
1330
1332

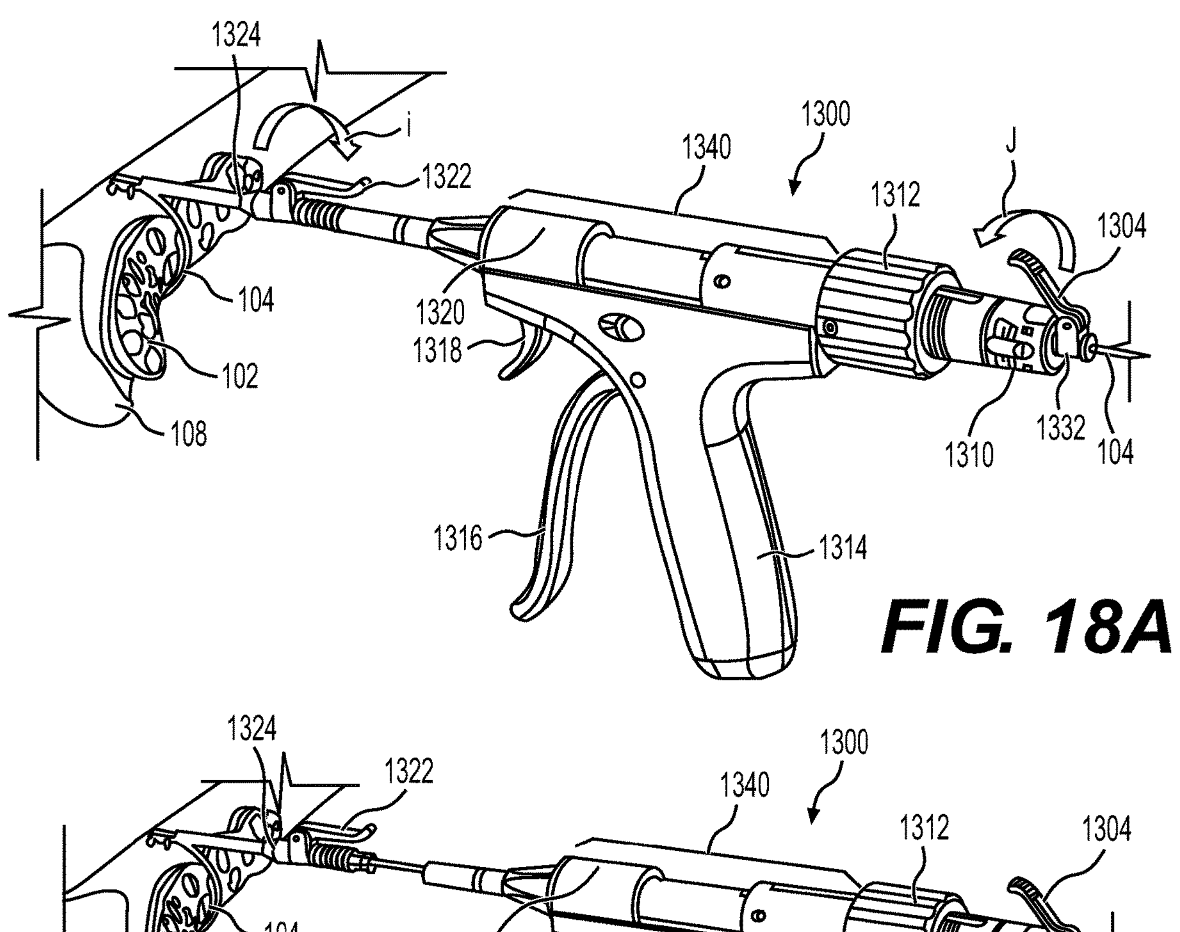
FIG. 18A
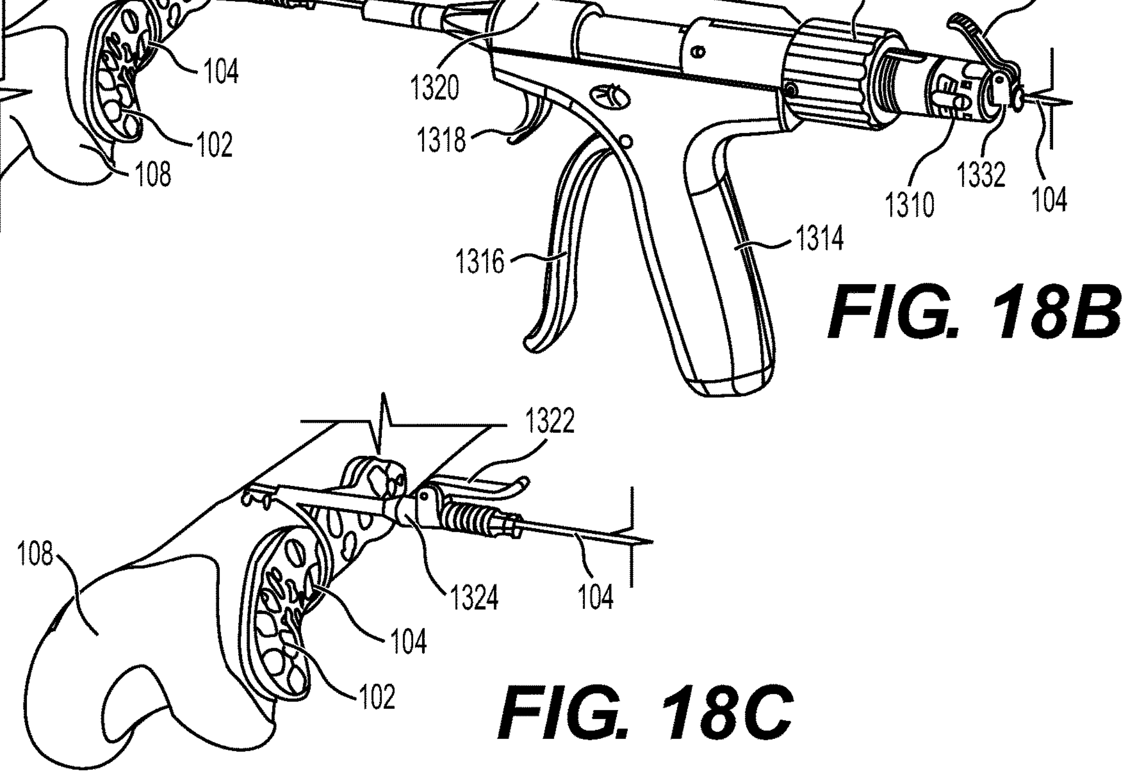
FIG. 18B
FIG. 18C

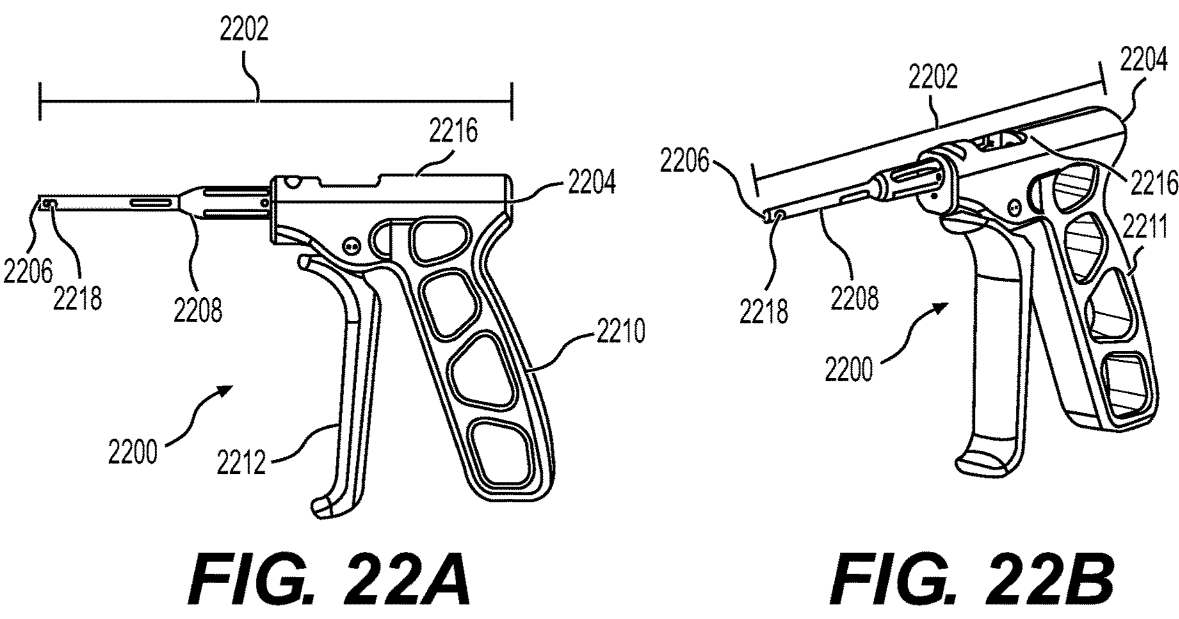
FIG. 22A
FIG. 22B
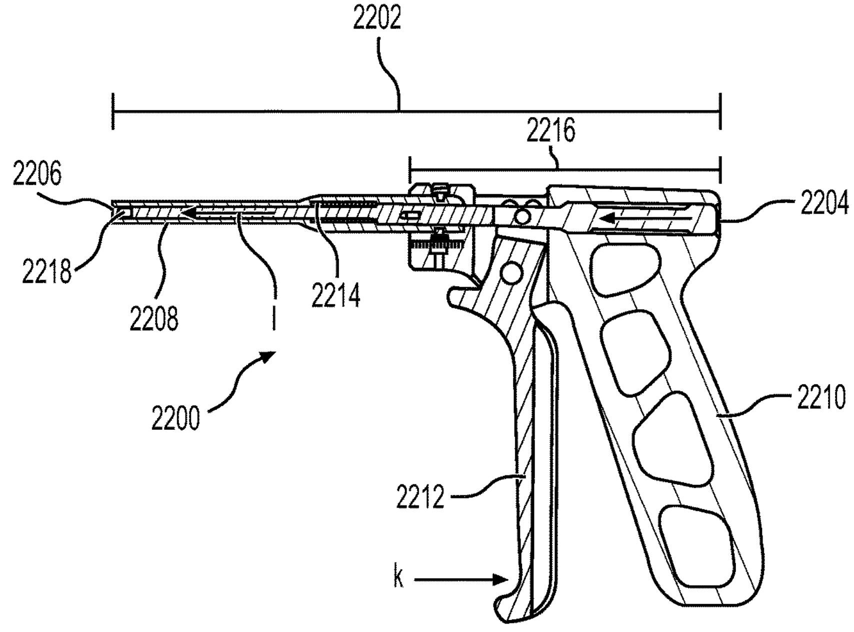
FIG. 22C

CERCLAGE CABLE SYSTEM AND APPARATUS

CROSS REFERENCE TO RELATED APPLICATIONS

This application is a divisional application of patent application Ser. No. 17/150,273 filed on Jan. 15, 2021, which is incorporated in its entirety herein.

BACKGROUND

Cerclage may be defined as a method of "strapping" stranded cables to the bone for the purpose of assisting in fixation of fractures. Fractured bones may often be surgically treated using cerclage techniques in which a wire or other cable may be wrapped around a portion of bone to facilitate fixation or repair thereof. In these surgical procedures, the cerclage cable may be used in combination with, for example, a bone or trauma plate, an intramedullary nail, or with a reduction tool to help secure and stabilize a bone. Additionally, fractures involving large bones may be difficult to immobilize, and often require the use of bone screws, cables and/or bone plates to securely reunite fractured bone segments. One frequently used procedure involves wiring the fractured bone to a plate that may be attached at multiple attachment points along the bone or other bony structure on either side of a fracture. The plate may be fastened to the bone using bone screws or bone spikes, and the attachment may be reinforced by encircling both the bone and the bone plate with cerclage cable. Generally, cerclage cable may be looped around the bone plate and may then be secured in position on the bone plate by threading the cable through an opening in a structure attached to the plate. The loop formed by the cerclage cable may then be tightened and the cerclage cable may be secured to itself by means of a deformation crimping device in order to maintain tension in the loop to prevent undesired movement or shifting of the cerclage cable or the underlying anatomical or surgical structure. Cerclage procedures generally involve looping a wire or cable around the bone to be repaired.

SUMMARY

A cerclage cable system and apparatus are disclosed herein. According to some embodiments, a cerclage cable system may comprise a bone plate, one or more securing devices, and one or more cerclage cables. The bone plate may comprise a plurality of bone plate apertures thereupon, wherein the bone plate may be configured to be affixed to a bone. The one or more securing devices may comprise a body comprising a proximal end and a distal end, wherein at least one securing device aperture may be disposed toward the proximal end, wherein the distal end of the securing device may be configured to be inserted into and received by the plurality of the bone plate apertures. The one or more cerclage cables may comprise two terminal ends, wherein the one or more cerclage cables may be wrapped around the bone, wherein one terminal end of the one or more cerclage cables may be passed through at least one securing device aperture.

In some embodiments, a cerclage cable system may comprise a bone plate, one or more securing devices, one or more cerclage cables, and a crimp. The bone plate may comprise a plurality of bone plate apertures thereupon, wherein the bone plate may be configured to be affixed to a bone. The one or more securing devices may comprise a body comprising a proximal end and a distal end, wherein the proximal end may comprise at least one securing device aperture, wherein the securing devices may be configured to be inserted into and received by the plurality of bone plate apertures. The one or more cerclage cables may comprise two terminal ends, wherein the one or more cerclage cables may be wrapped around the bone, wherein one terminal end of the one or more cerclage cables may be passed through the at least one securing device aperture. The crimp may comprise two parallel lumens, wherein the lumens may be configured to receive the terminal ends of the cerclage cable.

In some embodiments, a method may comprise positioning a bone plate over a bone having a fracture, wherein the bone plate may comprise a plurality of bone plate apertures thereupon. The method may further comprise inserting a device into at least one bone plate aperture, wherein the securing device may comprise a proximal end and a distal end, wherein the proximal end may comprise at least one securing device aperture, wherein the securing device may be configured to be inserted into and received by the bone plate apertures. The method may comprise wrapping a cerclage cable around the bone, wherein the cerclage cable comprises two terminal ends; and passing at least one terminal end of the cerclage cable through the at least one securing device aperture. The method may further comprise securing the two terminal ends of the cerclage cable with a crimp, wherein the crimp may comprise two parallel lumens, wherein the lumens may be configured to receive the terminal ends of the cerclage cable.

Apparatus for the cerclage cable system, including a cerclage cable tensioner, is also disclosed herein. According to some embodiments, a cerclage cable tensioner may comprise a body, a modular tip, a cam lock, a cam lock lever, a rotary actuator, a squeeze actuator, a tension release trigger, and a rear cam lock. The body may comprise a shaft having a proximal end and a distal end. The modular tip may be disposed at the distal end of the shaft and removably affixed thereto. The cam lock lever may be disposed adjacent to the modular tip, wherein the cam lock lever may control the locking and unlocking of the cam lock, wherein the cam lock may act on the cerclage cable. The rotary actuator may be threadably disposed toward the proximal end of the shaft, wherein the rotary actuator may be rotatable in opposite directions, wherein one direction may displace a threaded cylinder to apply tension to the cerclage cable, and wherein the opposite direction may retract the threaded cylinder, thereby decreasing tension to the cerclage cable. The squeeze actuator may be coupled to a linkage, wherein the linkage may drive a central shaft forward to apply tension to the cerclage cable. The tension release trigger may release a pawl that may prevent the central shaft from moving in one direction and thereby may release tension from the squeeze actuator. The rear cam lock may be disposed at the proximal end of the shaft, wherein the rear cam lock may secure the cerclage cable in the cerclage cable tensioner. The cerclage cable may be threaded through the shaft from the modular tip at the distal end and through the proximal end of the shaft.

According to some embodiments, a cerclage cable tensioner may comprise a body, a modular tip, a cam lock, a cam lock lever, a rotary actuator, a squeeze actuator, a tension release trigger, a rear cam lock, a rear cam lock lever, and a tension gauge. The body may comprise a shaft having a proximal end and a distal end. The modular tip may be disposed at the distal end of the shaft and removably affixed thereto. The cam lock lever may be disposed adjacent to the modular tip, wherein the cam lock lever may control the locking and unlocking of the cam lock, wherein the cam lock may act on the cerclage cable. The rotary actuator may be threadably disposed toward the proximal end of the shaft, wherein the rotary actuator may be rotatable in opposite directions, wherein one direction may displace a threaded cylinder to apply tension to the cerclage cable, and wherein the opposite direction may retract the threaded cylinder, thereby decreasing tension to the cerclage cable. The squeeze actuator may be coupled to a linkage, wherein the linkage may drive a central shaft forward to apply tension to the cerclage cable. The tension release trigger may release a pawl that may prevent the central shaft from moving in one direction and thereby may release tension from the squeeze actuator. The rear cam lock may be disposed at the proximal end of the shaft, wherein the rear cam lock may secure the cerclage cable in the cerclage cable tensioner. The tension gauge may indicate the amount of tension applied to the cerclage cable. The modular tip, cam lock, and cam lock lever may be detachable from the cerclage cable tensioner, wherein the modular tip, cam lock, and cam lock lever may comprise a modular tip assembly. The cerclage cable may be threaded through the shaft from the modular tip at the distal end and through the proximal end of the shaft.

According to some embodiments, a method may comprise passing a cerclage cable through a cerclage cable tensioner, wherein the cerclage cable tensioner may comprise: a body, a modular tip, a cam lock, a cam lever, a rotary actuator, a squeeze actuator, a tension release trigger, a rear cam lock, and a rear cam lock lever. The body may comprise a shaft having a proximal end and a distal end. The modular tip may be disposed at the distal end of the shaft and removably affixed thereto. The cam lock lever may be disposed adjacent to the modular tip, wherein the cam lock lever may control the locking and unlocking of the cam lock, wherein the cam lock may act on the cerclage cable. The rotary actuator may be threadably disposed toward the proximal end of the shaft, wherein the rotary actuator may be rotatable in opposite directions, wherein one direction may displace a threaded cylinder to apply tension to the cerclage cable, and wherein the opposite direction may retract the threaded cylinder, thereby decreasing tension to the cerclage cable. The squeeze actuator may be coupled to a linkage, wherein the linkage may drive a central shaft forward to apply tension to the cerclage cable. The tension release trigger may release a pawl that may prevent the central shaft from moving in one direction and thereby may release tension from the squeeze actuator. The rear cam lock may be disposed at the proximal end of the shaft, wherein the rear cam lock may secure the cerclage cable in the cerclage cable tensioner. The rear cam lock lever may control the locking and unlocking of the rear cam lock.

The method may further comprise locking the rear cam lock lever to secure the cerclage cable to the cerclage cable tensioner. The method may comprise applying tension to the cerclage cable with the squeeze actuator, the rotary actuator, or combinations thereof. The method may further comprise locking the modular tip in place with the cam lock lever and unlocking the rear cam lock lever. The method may further comprise detaching the modular tip, the cam lock, and the cam lock lever from the cerclage cable tensioner, wherein the modular tip, the cam lock and the cam lock lever may remain attached to the cerclage cable, wherein a provisional tension on the cerclage cable may be maintained, and wherein the modular tip, the cam lock, and the cam lock lever may comprise a modular tip assembly. The method may include removing the cerclage cable tensioner after detaching the modular tip assembly.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings, which are included to provide a further understanding of the disclosure and are incorporated in and constitute a part of this application, illustrate certain non-limiting embodiments of inventive concepts. In the drawings:

FIGS. 7A and 7B illustrate a top perspective view and a front view of a cerclage cable anchor configured to fit cannulated screws, according to some embodiments;

FIG. 7C illustrates a cross-sectional view of the cerclage cable anchor of FIGS. 7A and 7B seated in a bone plate, according to some embodiments.

FIGS. 9A, 9B, 9C, and 9D illustrate a top perspective view, a top view, a cross-sectional view, and a side plan view, of a cerclage cable button with a hexalobular drive feature, according to some embodiments;

FIGS. 18A, 18B, and 18C illustrate the operation of the modular tip cam lock of a cerclage cable tensioner, according to some embodiments;

FIGS. 22A, 22B, and 22C illustrate a side view, a side plan view, and a cross-sectional view, respectively, of a flush cutter, according to some embodiments;

DETAILED DESCRIPTION

Figure 1A:
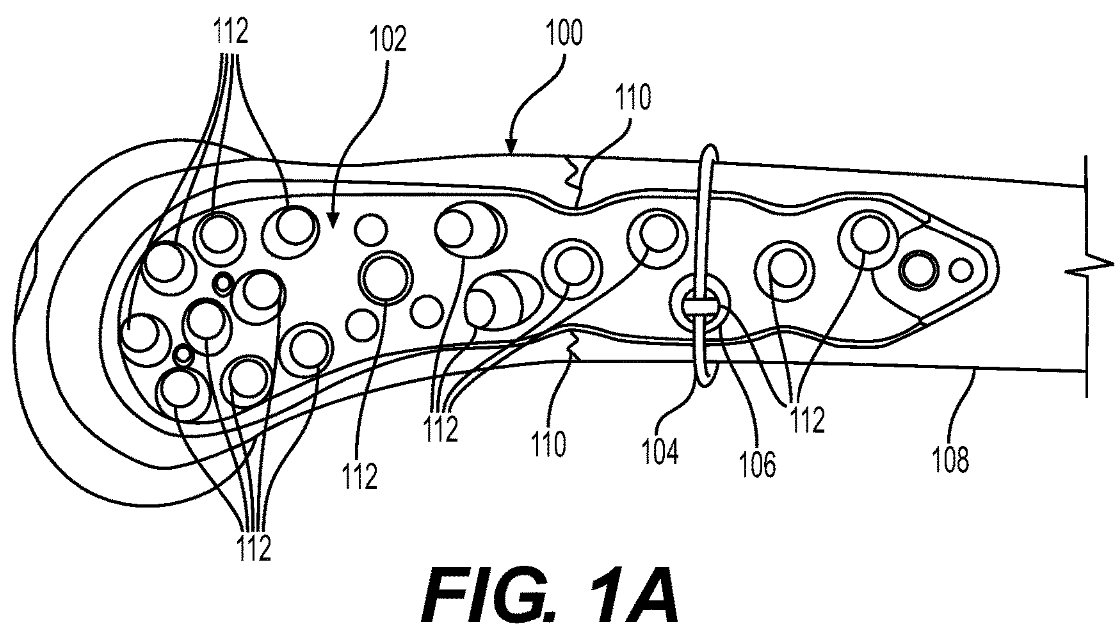
FIGS. 1A and 1B illustrate assembled cerclage cable systems, according to some embodiments.

It is to be understood that the present disclosure is not limited to particular devices or methods, which may, of course, vary. It is also to be understood that the terminology used herein is for the purpose of describing particular embodiments only and is not intended to be limiting. All numbers and ranges disclosed herein may vary by some amount. Whenever a numerical range with a lower limit and an upper limit is disclosed, any number and any included range falling within the range are specifically disclosed. Although individual embodiments are discussed herein, the invention covers all combinations of all those embodiments. As used herein, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected. If there is any conflict in the usages of a word or term in this specification and one or more patent or other documents that may be incorporated herein by reference, the definitions that are consistent with this specification should be adopted for the purposes of understanding this invention.

This disclosure relates to a cerclage cable systems and apparatus for internally positioning and retaining bone and bone fragments to facilitate healing. Embodiments of the cerclage cable systems disclosed herein may comprise a bone plate; one or more securing/attachment devices, wherein the securing/attachment devices may comprise cerclage cable anchors, cerclage cable buttons, or combinations thereof; one or more cerclage cables, and one or more crimps. The cerclage cable anchors or cerclage cable buttons, may engage with the cerclage cable and constrain its motion relative to the bone plate, bone, or any boney structure, in areas where the cerclage cable may be prone to slide along the length of the bone or boney structure, or otherwise deviate from the intended location. Embodiments of the cerclage cable apparatus disclosed herein may comprise a cable passer, a cable tensioner, a crimp tool, a flush cutter, and sterile packaging for the cerclage cable.

Cerclage Cable System

The bone plate may be attached to a bone having a fracture to assist in reducing and subsequently healing the fracture. Generally, reducing the fracture may include realigning and positioning the fractured portions of the bone to their original position or a similar stable position. In addition, fixing the fracture with the bone plate may include positioning the bone plate over the fractured area of the bone and securing the bone plate to the bone across the fracture. Bone plates may be configured to hold the bone in place while the fracture heals. Additionally, the bone plate may also provide support and/or compression to the bone in order to compress the fracture. Generally, the bone plate may include a plurality of apertures therein. The apertures may be configured to receive securing/attachment devices which may be inserted into the bone to secure the bone plate to the bone, wherein the securing/attachment devices may include, but may not be limited to, cerclage cable anchors, screw-head cerclage cable anchors, threaded cable anchors, cerclage cable buttons, and cerclage threaded cable eyelets.

Cerclage cable anchors may be used when cables are applied over a bone plate to provide fixation. Cerclage cable anchors may minimize, decrease, or prevent motion of cerclage cables along the length of the bone plate. In some embodiments, cerclage cable anchors may comprise a proximal end and a distal end, wherein a single aperture may be disposed at the proximal end, and wherein the distal end may be comprised of compressible fingers that may be compressed during insertion into an aperture of the bone plate and may expand after insertion into the aperture of the bone plate to provisionally lock in place while the cerclage cable is threaded through the single aperture of the cerclage cable anchor. In some embodiments, the compressible fingers may comprise a single groove disposed thereupon, wherein the groove may be configured to lock and catch in an aperture of the bone plate, thereby locking the cerclage anchor in place. In some embodiments, the compressible fingers may comprise a plurality of grooves disposed thereupon, wherein the plurality of grooves may be configured to lock and catch in the apertures in the bone plate. Essentially, the cerclage cable anchors may be pressed or snapped into the bone plate apertures. Cerclage cable anchors may be configured to fit both threaded and non-threaded bone plate apertures. More specifically, the cerclage cable anchors disclosed herein may be pressed or snapped into either threaded or non-threaded bone plate apertures.

In some embodiments, the cerclage cable anchor may be a screw-head cerclage cable anchor having a proximal end and a distal end, wherein a screw may be threadably attached at the proximal end, and wherein an anchor comprising compressible fingers may be disposed toward the distal end. The anchor may comprise a threaded aperture disposed toward the proximal end configured to threadably receive the screw. The compressible fingers may be compressed during insertion into a bone plate aperture and may expand after insertion into the bone plate aperture to provisionally lock in place. The top, center of the screw head may be configured to receive a hexagonal driver, wherein two (2) or more apertures may be disposed about the perimeter of the screw head, wherein the apertures may be configured to receive a cerclage cable. The screw may be used to lock the screw-head cerclage anchor into place, while the cerclage cable may be threaded through the apertures disposed about the perimeter of screw head.

In some embodiments, the cerclage cable anchor may be a threaded cable anchor or eyelet. In some embodiments, the cerclage cable anchor may be configured to receive a minor diameter hexalobe driver. In some embodiments, the cerclage cable anchor may be configured for insertion into cannulated screws, wherein the distal end of the cerclage cable anchor may be inserted into the head of the cannulated screw.

In some embodiments, the cerclage cable anchor may be a cerclage cable button, wherein cerclage cable buttons may be threaded devices that may feature conical threads which may interface with apertures in the cerclage bone plate, wherein the apertures are locking apertures. The cerclage cable button may comprise a hexalobular drive feature which may interface with an appropriate driver. Drive size may vary to match the size of the threaded aperture in the cerclage bone plate. There may be two (2) or more equally spaced apertures disposed about the perimeter toward the proximal end of the cerclage cable button, thereby permitting passage of the cerclage cable. The cerclage cable may pass through the cerclage cable button, entering through one of the apertures, and exiting out of a second of the apertures. Two (2) or more apertures may provide a plurality of different cable routing combinations. For example, a cerclage cable button comprising three (3) apertures may provide three (3) different routing combinations, spaced 120 degrees apart. Cerclage cable buttons may be cannulated to permit the passage of a k-wire through their center or, for example, holding or stabilizing the device in a graphic case for washing or sterilizing.

It should be noted that the securing/attachment devices disclosed herein may be constructed from a variety of metallic alloys, including, but not limited to, stainless steel, cobalt chromium, titanium groups, and combinations thereof. The selection of the alloy varies to suit the bone plate in which the securing/attachment devices interface.

Cerclage cables may be bundles of wires arranged and twisted into groups, wherein the wire is the smallest element of the cable, wherein the group of wires form a strand, and wherein a group of strands form a cable. Wire size, wire count, strand count, as well as the direction and pitch of each strand or cable may be varied to yield different properties. As disclosed herein, some embodiments may comprise a (1×19)+8(1×7) configuration. This configuration may be comprised of one center core strand comprising 19 wires (1×19) and 8 outer strands comprising 7 wires, 8(1×7) for a total of 75 individual wire elements. All wire elements may be the same size but may be varied to yield different properties. Generally, cables may be comprised of metallic wires, but may use combinations of different alloys to yield varying properties or may be comprised partially or completely of polymeric materials. Suitable metallic alloys include, but are not limited to ASTM F136, F1472, F1295, F138, F1314, F90, F1537, F1058, or F562. Suitable polymer alloys may include, but are not limited to, ASTM F848 and polyethylene terephthalate.

Cerclage cables may be manufactured in continuous lengths, cut to length, and then terminated to add functionality and prevent unraveling. As disclosed herein, some embodiments of cerclage cables may have terminations comprising a bead on one end and a swage on the opposite end. The bead may be formed by locally melting the cable and relying on the surface tension of the liquid metal to form a spherical bead. Subsequently, the bead, as formed, may be fully adhered to each individual wire element. It should be noted that the ball end may also be formed by swaging or crimping a machined ball onto the cable. The ball may be an attachment point for a crimp. The ball end may also be formed by swaging or crimping a machined ball onto the cable. The swage may be formed similarly, by locally melting the cable. In addition to the local melting of the cable, the swage end may be later compressed and deformed by tooling to form a smooth surface, which may be smaller in diameter than the cable itself. The decreased or tapered diameter may aid with inserting the cable into a lumen on a crimp device.

As disclosed herein, a crimp may be a crushable or deformable metallic device used to lock the tension of the cerclage cable in situ. The crimp may be comprised of two parallel lumens which may permit the entry of both ends of a single cable and tapered legs, wherein the tapered legs may be configured to maintain alignment of the crimp and guide the crimp in place. The crimp may feature tines on each corner which may minimize, decrease, or prevent motion on the bone surface by biting into the bone during tensioning and positioning. The crimp may comprise a waist-like shape which may help to align a crimping tool to the crimp. Crimps may be constructed from a variety of metallic alloys, including, but not limited to, stainless steel, cobalt chromium, titanium, titanium groups, and combinations thereof. The selection of the alloy varies to suit cerclage cable system in which the crimp interfaces. The dimension of the crimps may vary, depending upon the application. For example, the crimp dimensions may range in length from 3-15 mm, they may range in width from 3-15 mm and they may range in height from 2-12 mm.

Cerclage Cable Apparatus

The cerclage cable passer may be used to guide the cerclage cable around the bone. Typically, access to the bone may be limited to one side. The surgeon may require an incision on one side of the bone and may then insert a cable passer through the incision and around the bone. Once the cerclage cable passer is around the bone, the cerclage cable may be inserted into one end of the cerclage cable passer channel or tube, then threaded through, exiting on the opposite end of the cerclage cable passer channel or tube. Once the cerclage cable is through the cerclage cable passer, the surgeon may pull the cable through and remove the cerclage cable passer, leaving the cerclage cable around the bone. Embodiments of cerclage cable passers may include a range of sizes and various angled offsets. For example, according to some embodiments disclosed herein, cerclage cable passers may be straight, specifically offset, variably offset, include a varying radius, or include multiple bend radii. As further disclosed herein, a variable bend radius cable passer may optimize the bend radius to match the bone contour. This may improve fit, reduce soft tissue disruption, and improve safety. For example, the variable bend radius passer has multiple bend radii that are used to define a passer shape that more closely resembles the cross section of the bone. The multiple bend radii may include a primary ben radius and a secondary bend radius, the primary bend radius may be between 10-60 mm and the secondary bend radius may be between 5-50 mm. By better approximating the shape of the bone, the variable bend radius allows a closer fit when passing the cable around the bone to reduce soft tissue disruption and may also reduce the chance of inadvertently capturing or "hooking" soft tissue, such as an artery, veins, or other neurovascular structure. Preferably, the cable passer will be made from cannulated stainless steel and will be connected to an ergonomic silicone handle.

After the cerclage cable is wrapped around the bone and through the crimp, the cerclage cable tensioner may apply force to one end of the cerclage cable while holding the crimp in place. The applied force may pull the cerclage cable through the crimp, thereby compressing any bone fragments while stabilizing the bone fracture. As disclosed herein, the cerclage cable tensioner may be a dual-action tensioner, comprising both rotary and squeeze actuated tensioning elements. The cerclage cable tensioner may be equipped with a cam lock and cam lock lever that may hold the cable while force may be applied. The rotary actuator, when rotated, may displace a threaded tube to apply tension to the cerclage cable. The squeeze actuator may allow the user to quickly decrease slack and apply tension. The squeeze actuator may be connected to a linkage that may drive a central shaft forward to apply tension to the cerclage cable. The user may pull a trigger, wherein the trigger may release a pawl that may prevent the central shaft from moving in one direction to release tension from the squeeze actuator. Tension may also be released by opening the cam lock lever to allow the cerclage cable to move freely. In some embodiments, the tensioner may be comprised of a modular tip that may be used to lock the cerclage cable with provisional tension, wherein the modular tip, the cam lock, and the cam lever may form a modular tip assembly. While connected to the cerclage cable, the modular tip assembly may be detached from the cerclage cable tensioner to maintain provisional tension on the cerclage cable.

Generally, the method of operating a tensioner may comprise passing the cerclage cable through the tensioner; locking the rear cam lock lever to secure the cerclage cable to the tensioner; manually pulling the cable (by hand) to tighten the cerclage cable; locking the modular tip in place with the cam lock lever; unlocking the rear cam lock lever; and removing the cerclage cable tensioner, wherein the modular tip, cam lock, and cam lock lever may be detached for the purpose of maintaining tension on the cerclage cable. The detachable modular tip, cam lock, and cam lock lever may comprise the modular tip assembly.

The crimp tool may be used to deform the crimp around the cerclage cable and lock tension on the bone. The crimp tool may be a four-bar linkage that may multiply the force applied at the handles to deform the crimp. The crimp tool may feature a ratchet and pawl that may prevent under crimping of the deformable crimp and prevent variability in crimping between operators. Moreover, the crimp tool may require the crimp to completely travel to the closed position before returning to the open position in order to prevent inadequate or insufficient crimping. As disclosed herein, the crimp tool comprises a nose, wherein the nose extends from a length of about 30 mm to about 60 mm. The width of the jaws of the crimp tool are preferably reduced for percutaneous applications. In some embodiments, the width of the jaw range from 30-50 mm. In some embodiments, an auxiliary handle may be substituted for users having smaller hands due to the crimp tool's required travel and closure.

A flush cutter may be used to cleanly cut and remove any excess cable after the cerclage cable has been tensioned and crimped. The flush cutter may comprise a modular blade cartridge having an aperture, wherein the aperture may be sized to accept the cerclage cable. Once the cerclage cable is passed through the aperture, the flush cutter blade cartridge may be pushed or positioned firmly against the face of the crimp for the purpose of making the cut as close to the crimp as possible. Once the flush cutter and the blade cartridge are positioned, a surgeon may squeeze the trigger of the flush cutter to actuate the blade, wherein the blade may cleanly shear the cerclage cable, thereby leaving essentially no sharp edges or protrusions of cerclage cable wires that may irritate soft tissue.

Embodiments disclosed herein also include a sterile packaging assembly for metallic or polymeric cerclage cables used for fixation of bone fractures, as disclosed herein. The sterile packaging assembly comprises at least three layers of packaging, including, but not limited to an outer thermoformed plastic tray and lid; an inner thermoformed plastic tray and lid; and a thermoformed plastic cable spool comprising a pair of identical half-spools.

The cerclage cable may be positioned inside the cable spool. The cable spool may be sealed inside of the inner tray. The inner tray may be sealed inside of the outer dray. The double-tray configuration may provide the ability for aseptic presentation into the sterile filed in addition to a robust sterile barrier. The inner cable spool may comprise the cerclage cable, thereby providing ease of dispensing by the end user. The inner spool may comprise a pair of interlocking features that keep the spool together, and a pair of guiding features for maintaining alignment of the cerclage cable. Once assembled, the halves may form a ring-like center cavity that may house the cerclage cable. The cable spool may have a pair of openings in which the cerclage cable may exit for dispensing. The inner spool not only protects the cerclage cable from shipping damage and damage to the sterile barrier, but also provides a novel method of dispensing the cerclage cable intra-operatively.

The packaging materials may be comprised of PETG trays and Tyvek lids. The dimensions of the outer thermoformed plastic tray and lid may range in L×W×H from about 50-400 mm×50-400 mm×10-100 mm. The dimensions of the inner thermoformed plastic tray and lid may range within about the same range of the outer tray and lid but will be smaller when compared to the outer tray and lid. The thermoformed plastic cable spool may have a diameter ranging from about 20 mm to about 150 mm. It should be noted that the dimensions of the packaging assembly may be less than greater than the dimensions disclosed herein.

In accordance with the present disclosure, a method of repairing a fractured bone using a cerclage cable system, according to some embodiments, may comprise positioning a bone plate over a bone having a fracture, wherein the bone plate may comprise a plurality of bone plate apertures thereupon. The method may also provide inserting a securing device into at least one bone plate aperture, wherein the securing device may comprise a proximal end and a distal end, wherein the proximal end may comprise at least one securing device aperture, wherein the securing device may be configured to be inserted into and received by the bone plate apertures. The method may further provide wrapping a cerclage cable around the bone, wherein the cerclage cable may comprise two terminal ends; passing at least one terminal end of the cerclage cable through the at least one securing device aperture. The method may further provide securing the two terminal ends of the cerclage cable with the crimp, wherein the crimp may comprise two parallel lumens, wherein the lumens may be configured to receive the terminal ends of the cerclage cable. The method may further comprise tightening the cerclage cable with a tensioner; cutting excess portions of the cerclage cable with a flush cuter; and deforming the crimp with a crimp tool.

In accordance with the present disclosure, a method of applying tension to a cerclage cable used in a bone fracture stabilization procedure may comprise passing a cerclage cable through a cerclage cable tensioner, wherein the cerclage cable tensioner may comprise: a body, a modular tip, a cam lock, a cam lever, a rotary actuator, a squeeze actuator, a tension release trigger, a rear cam lock, and a rear cam lock lever. The body may comprise a shaft having a proximal end and a distal end. The modular tip may be disposed at the distal end of the shaft and removably affixed thereto. The cam lock lever may be disposed adjacent to the modular tip, wherein the cam lock lever may control the locking and unlocking of the cam lock, wherein the cam lock may act on the cerclage cable. The rotary actuator may be threadably disposed toward the proximal end of the shaft, wherein the rotary actuator may be rotatable in opposite directions, wherein one direction may displace a threaded cylinder to apply tension to the cerclage cable, and wherein the opposite direction may retract the threaded cylinder, thereby decreasing tension to the cerclage cable. The squeeze actuator may be coupled to a linkage, wherein the linkage may drive a central shaft forward to apply tension to the cerclage cable. The tension release trigger may release a pawl that may prevent the central shaft from moving in one direction and thereby may release tension from the squeeze actuator. The rear cam lock may be disposed at the proximal end of the shaft, wherein the rear cam lock may secure the cerclage cable in the cerclage cable tensioner. The rear cam lock lever may control the locking and unlocking of the rear cam lock.

The method may further comprise locking the rear cam lock lever to secure the cerclage cable to the cerclage cable tensioner. The method may comprise applying tension to the cerclage cable with the squeeze actuator, the rotary actuator, or combinations thereof. The method may further comprise locking the modular tip in place with the cam lock lever and unlocking the rear cam lock lever. The method may further comprise detaching the modular tip, the cam lock, and the cam lock lever from the cerclage cable tensioner, wherein the modular tip, the cam lock and the cam lock lever may remain attached to the cerclage cable, wherein a provisional tension on the cerclage cable may be maintained, and wherein the modular tip, the cam lock, and the cam lock lever may comprise a modular tip assembly. The method may include removing the cerclage cable tensioner after detaching the modular tip assembly.

In accordance with the present disclosure, a sterile packaging of a cerclage cable, according to some embodiments, may comprise positioning a cerclage cable inside a cable spool, wherein the cable spool is a thermoformed plastic cable spool comprising a pair of identical half-spools, wherein the cable spool comprises a pair of interlocking features that connect the two half-spools and a pair of guiding features that maintain alignment of the cerclage cable. The method further comprises sealing the cable spool inside of an inner tray and sealing the inner tray inside of an outer tray.

Figure 1B:
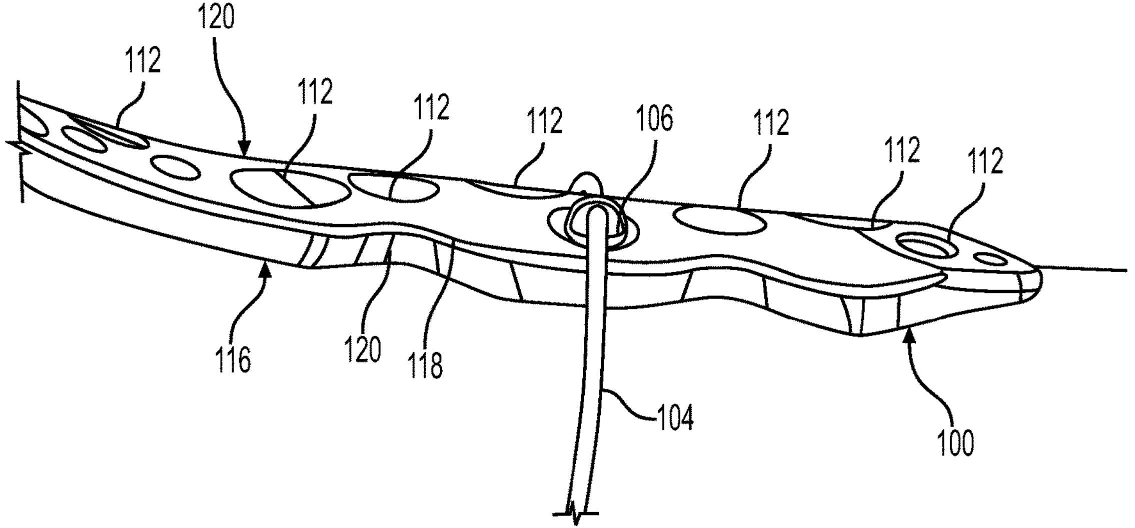

Referring now to FIG. 1A, which illustrates an assembled cerclage cable system 100 attached to a bone 108, comprising a bone plate 102, a securing/attachment device 106, and a cerclage cable 104. Cerclage cable system 100 may be secured to bone 108 by cerclage cable 104 and securing/attachment device 106. Securing/attachment device 106 may be secured to bone plate 102. Cerclage cable system 100 may be secured to bone 108 to hold bone fracture 110 or fragments of bone in place until bone 108 heals. As shown, bone plate 102 comprises bone plate apertures 112 for receipt of securing/attachment devices 106. Bone plate apertures 112 are illustrated as generally cylindrical; however, bone plate apertures 112 may include any desired shape, such as conical, spherical, polygon, elliptical, or combinations thereof. For example, bone plate apertures 112 that are spherical shaped may be used for receipt of spherical-shaped securing/attachment devices 106. The curvature or shape of the bone plate 102 may be configured to conform to the shape of the bone 108. As illustrated in FIG. 1B, securing/attachment device 106 may be secured to bone plate 102 by bone plate apertures 102. Cerclage cable 104 may be secured to bone plate 102 by use of securing/attachment device 106, as discussed in greater detail below.

Referring to FIGS. 1A and 1B, bone plate 102 may include bone contacting surface 116 and surface opposite bone contacting surface 118. Bone plate 102 may define bone plate height 120 as the distance between bone contacting surface 116 and opposite surface 118. As illustrated, bone contacting surface 116 and opposite surface 118 may each have contour and may not be substantially flat. Bone contacting surface 116 and opposite surface 118 may be non-parallel and may have divergent surfaces. It should be noted that bone plate 102 may be secured in other locations and to other types of bones in accordance with this disclosure. For example, bone plate 102 may be secure to a femur, the tibia, pelvis, humerus, ulna, radius, tarsus, metatarsus, scapula, clavicle, fibula, talus, vertebral bodies, and phalanges.

Bone plate 102 may be constructed of any biocompatible ceramic or metal, including, but not limited to, a titanium alloy, cobalt, chromium, cobalt chromium molybdenum, porous tantalum, or highly porous biomaterial. A highly porous biomaterial may be useful as a bone substitute and may be a cell and tissue receptive material. Bone plate 102 may take several forms, such as a periarticular plate, which may be surrounding a joint, or a non-contact bridging plate, where spacers may be used to hold the non-contact bridging plate off of bone 108.

Figure 2A:
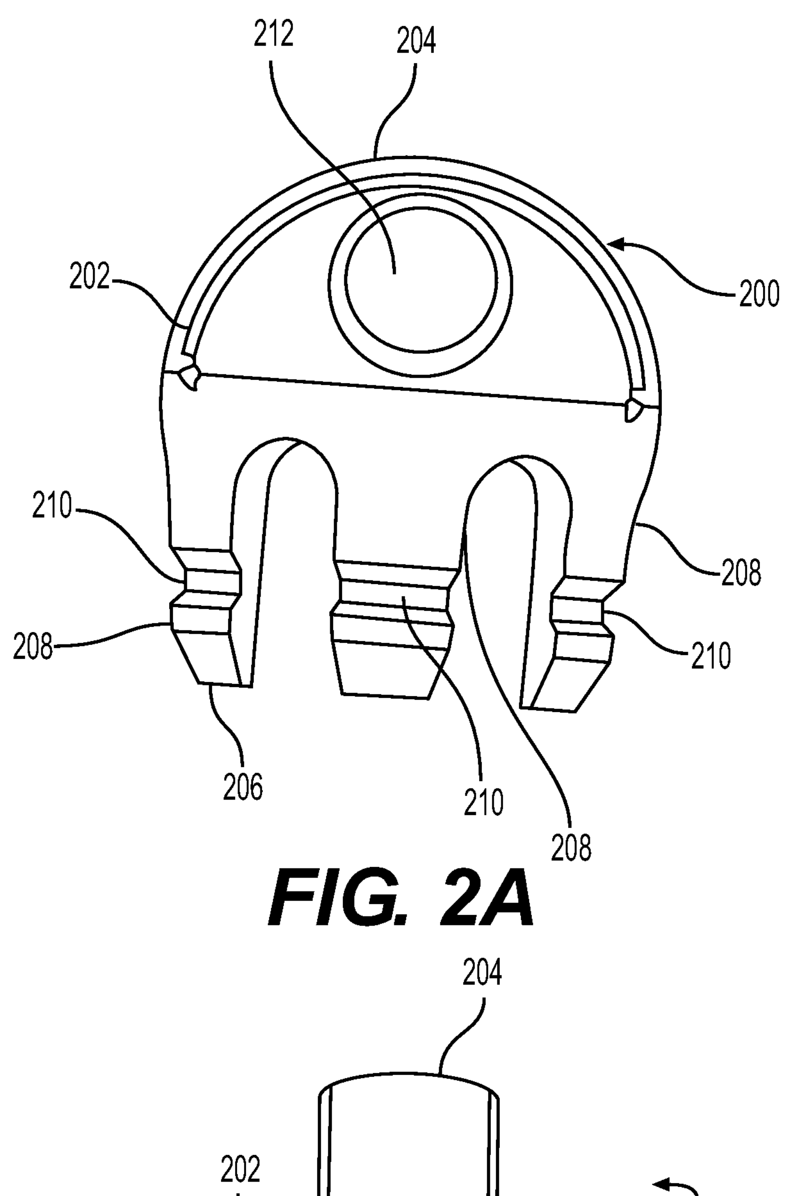
FIGS. 2A and 2B illustrate a front view and a side view, respectively, of a compressible, single-grooved cable anchor, according to some embodiments.
Figure 2B:
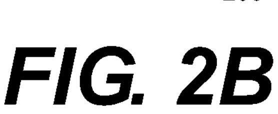

FIGS. 2A and 2B illustrate a front view and a side view, respectively, of a compressible, single-grooved cable anchor 200, according to some embodiments. The single-grooved cable anchor 200 may comprise a body 202 having a proximate end 204 and a distal end 206. Compressible fingers 208 may be located about the distal end 206, wherein the compressible fingers 208 comprise at least a single groove 210. As illustrated, the single groove 210 may be oriented perpendicular with respect to a longitudinal axis of the respective compressible finger 208. A single aperture 212 may be disposed about the proximate end 204. Single-grooved cable anchor 200 may be secured to bone plate 102.

Figure 3A:
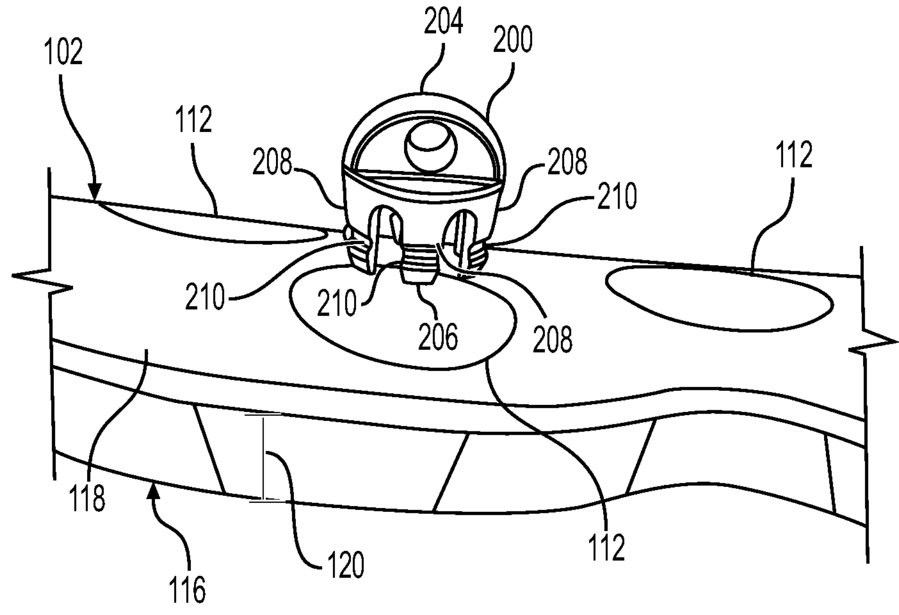
FIGS. 3A and 3B illustrate the positioning and insertion, respectively, of a compressible, single-grooved cable anchor into a bone plate, according to some embodiments.
Figure 3B:
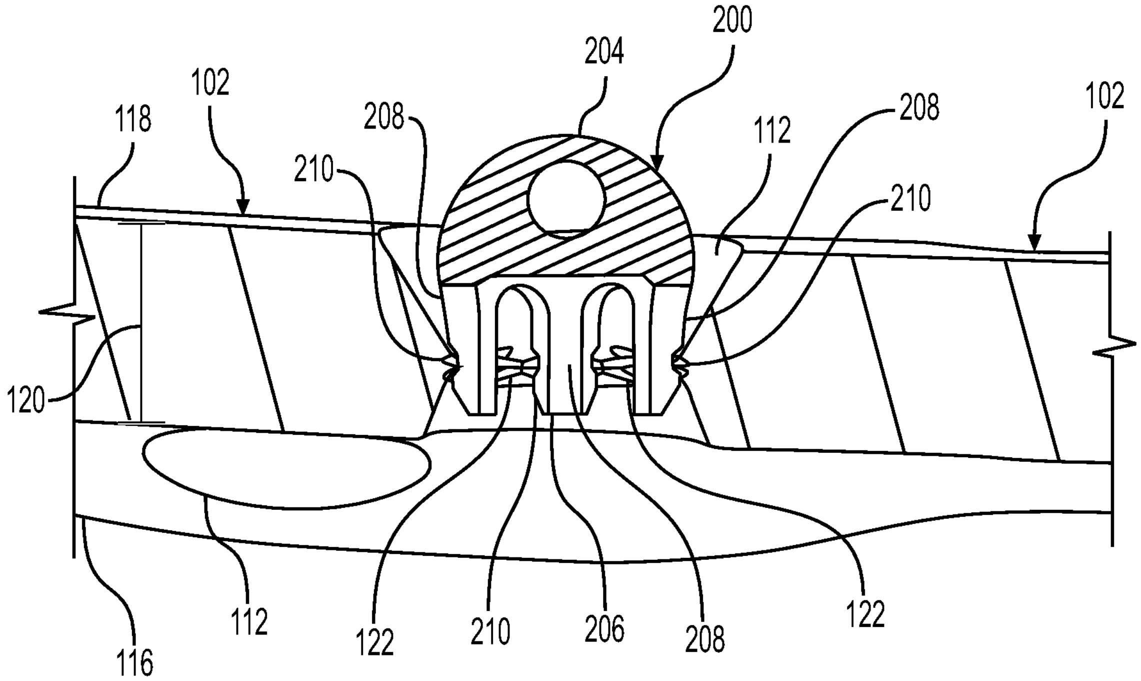

FIGS. 3A and 3B illustrate the positioning and insertion, respectively, of a compressible, single-grooved cable anchor 200 into a bone plate 102, according to some embodiments. Single-grooved cable anchor 200 may be secured to bone plate 102 through bone plate aperture 112. As shown, in some embodiments, single-grooved cable anchor 200 may be connected to bone plate 102 via bias, lock, and catch mechanisms. Compressible fingers 208 may be biased inwards when pressed through aperture 112 and the groove catches and releases on the shoulder portion 122 in the aperture 112 which extends radially inwardly from the wall of the aperture 112. This can best be seen in FIG. 3B.

Figures 4, 5A, 5B:
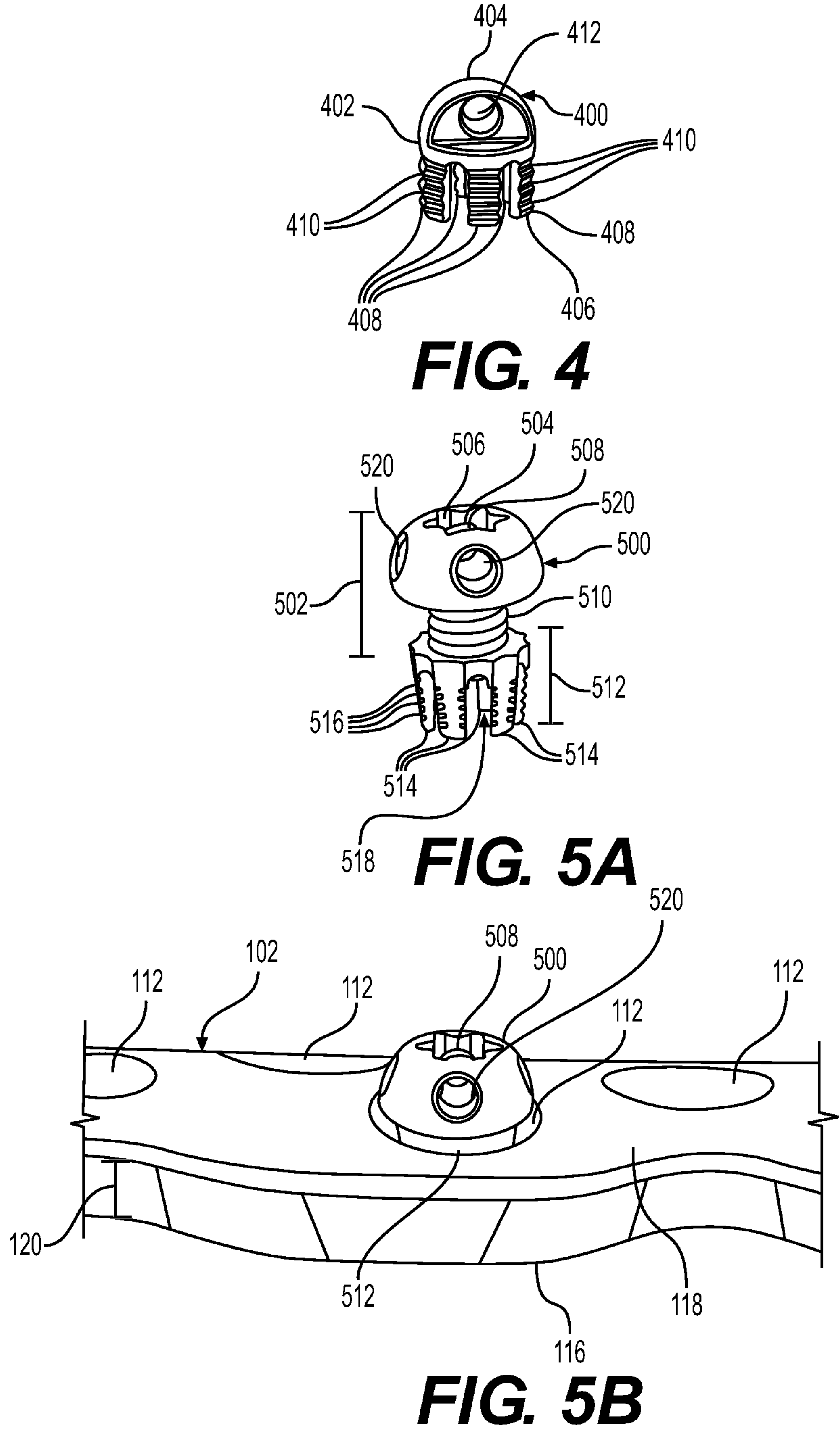
FIG. 4 illustrates an alternative configuration of a compressible, multi-grooved cerclage cable anchor, according to some embodiments.
FIG. 5A illustrates a compressible cerclage screw-head cable anchor, according to some embodiments.
FIG. 5B illustrates the compressible cerclage screw-head cable anchor of FIG. 5A seated in a bone plate, according to some embodiments.

FIG. 4 illustrates a cable anchor 400, which is substantially similar to single-grooved cable anchor 200, with the exception of differences disclosed herein. Cable anchor 400 may comprise body 402 having proximate end 404 and distal end 406. Compressible fingers 408 are located about distal end 406, wherein the compressible fingers may comprise two or more grooves 410. A single aperture 412 may be disposed about the proximate end 404. Cable anchor 400 may be secured to bone plate (not shown). Cable anchor 400 may be pressed into bone plate aperture 112. The compressible fingers 408 may be compressed during insertion and may expand to provisionally lock in place while the cerclage cable 104 may be threaded through aperture 412.

FIGS. 5A and 5B illustrate a compressible screw-head cable anchor 500, and the compressible screw-head cable anchor 500 seated in bone plate 102, respectively, according to some embodiments. Screw-head cable anchor 500 may be comprised of screw 502 having polygon or hex opening 504, polygon or hex socket 506, screw-head cavity 508, and threads 510. Screw head cable anchor 500 further comprises anchor 512 comprising compressible fingers 514 having two or more grooves 516 and screw cavity 518. Referring to FIG. 5A, screw-head cable anchor 500 may be pressed into bone plate aperture 112 and screw head 502 may lock anchor 512 into place while cerclage cable (not shown) may be threaded through apertures 520 in screw head 502. Compressible fingers 514 may compress during insertion and expand as screw 502 is advanced, thereby locking screw-head cerclage anchor 500 into position, as shown in FIG. 5B.

Figures 6A, 6B:
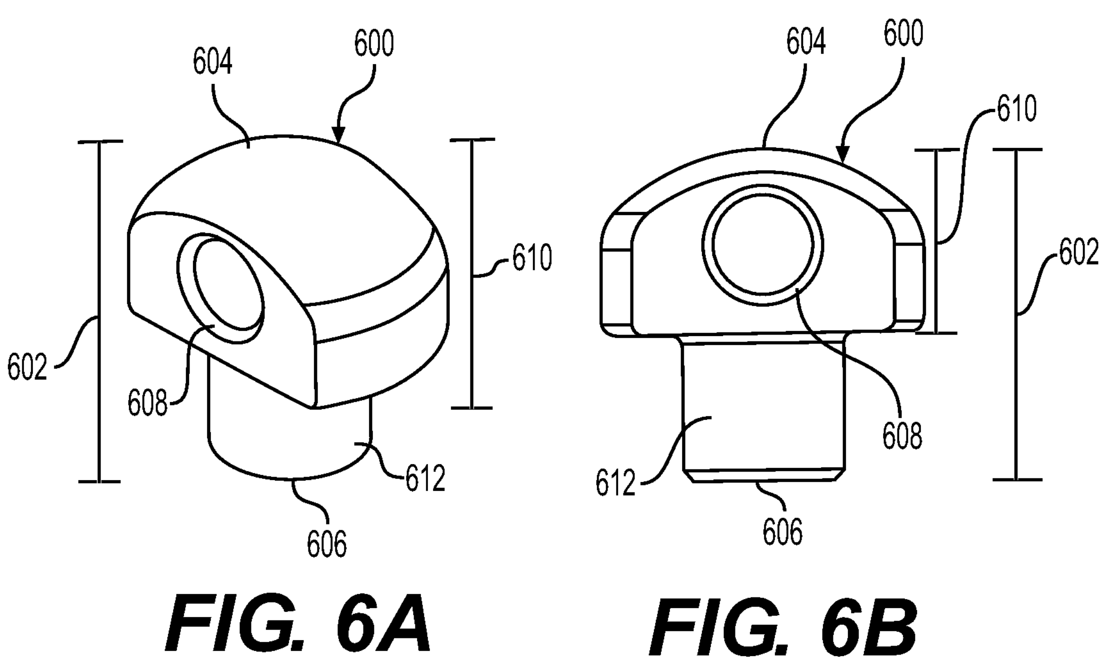
FIGS. 6A and 6B illustrate a top perspective view and a front view, respectively, of a cerclage cable anchor configured to fit a hexalobe drive with a minor diameter, according to some embodiments.
Figure 6C:
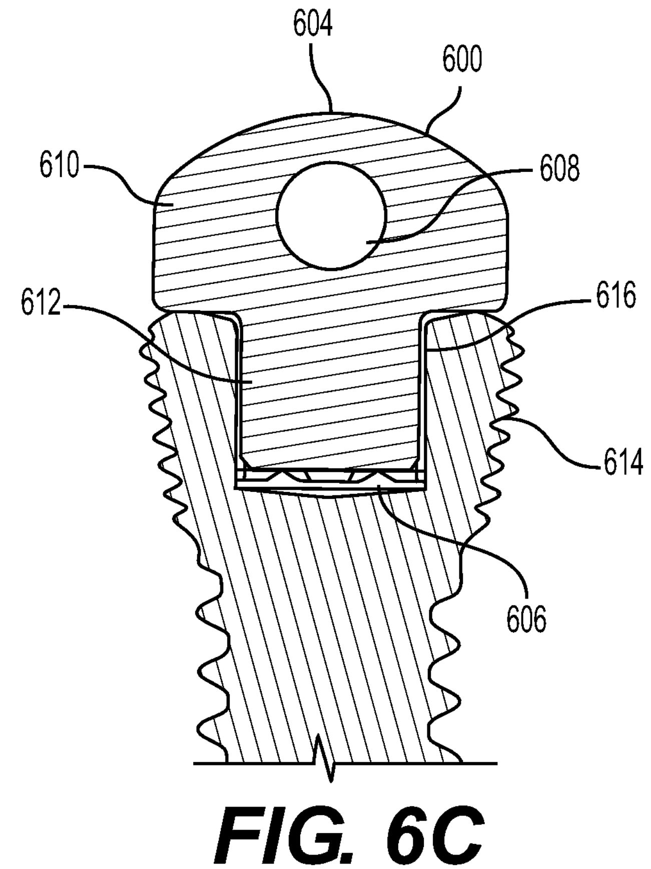
FIG. 6C illustrates a cross-sectional view of the cerclage cable anchor of FIGS. 6A and 6B seated in a bone plate, according to some embodiments.

FIGS. 6A, 6B, and 6C illustrate a top perspective view, a front view, and a cross-sectional view seated in screw head 614, respectively, of a cable anchor 600 configured to fit a hexalobe drive with a minor diameter, according to some embodiments. Cable anchor 600 is comprised of body 602, comprising proximate end 604 and distal end 606. As illustrated, aperture 608 may be disposed about proximate end 604 through head 610. In addition, extension 612 extends to distal end 606.

FIGS. 7A, 7B, and 7C illustrate a top perspective view, a front view, and a cross-sectional view seated in screw head 716, respectively, of a cannulated cable anchor 700 configured to fit cannulated screws, according to some embodiments. Cannulated cable anchor 700 comprises a body 702 comprising a proximate end 704 and a distal end 706. As illustrated, aperture 708 may be disposed about proximate end 704 through head 710. Cannulated cable anchor 700 further comprises first extension 712 and second extension 714, wherein first extension 712 extends from head 710 to second extension 714, and wherein second extension extends from first extension 712 to distal end 706.

Figures 8A, 8B, 8C:
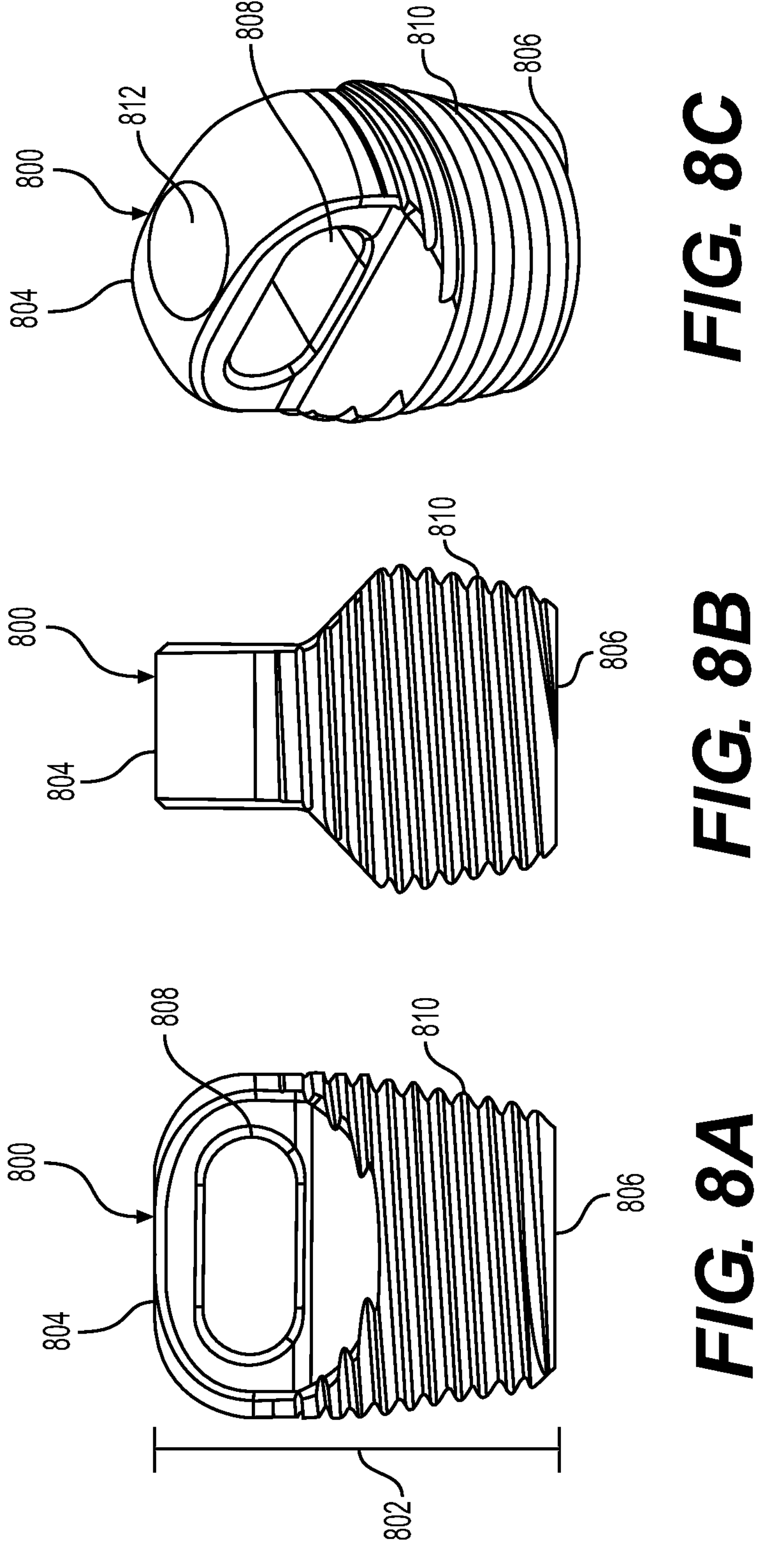
FIGS. 8A, 8B, and 8C illustrate front, side, and top perspective views of a threaded cerclage cable anchor, according to some embodiments.

FIGS. 8A, 8B, and 8C illustrate front, side, and top perspective views of a threaded cable anchor 800, according to some embodiments. Threaded cable anchor 800 may be comprised of body 802, having proximal end 804 and distal end 806. Aperture 808 may be disposed about proximal end 804 and indention 812 may disposed atop proximal end 804. Threads 810 may be disposed about body 800 at least toward proximal end 804.

FIGS. 9A, 9B, 9C, and 9D illustrate a top perspective view, a side perspective view, a top view, and a cross-sectional view of a hex cable button 900 with a hexalobular drive feature, respectively, according to some embodiments. Hex cable button 900 may be comprised of body 902, which may define threading 904. Hex cable button 900 may also comprise apertures 906, polygon opening 908 (e.g., a hexagon opening as shown), and polygon socket 910 (e.g., a hexagon socket as shown). Cavity 912 may be defined inside hex cable button 900. Threading 904 may be configured to align with bone plate threading (not shown). In some embodiments, cavity 912 may be in communication with apertures 906, hex opening 908, and hex socket 910. Apertures 906 may also be configured to receive cerclage cable as previously shown in FIGS. 1A and 1B.

There may be a plurality of apertures 906, such as from 1 to 6 apertures, 1 or more apertures, 2 or more apertures, 3 or more apertures, 4 or more apertures, 5 or more apertures, or 6 or more apertures. Hex cable button 900 may define more than two cable apertures 906 in order to provide a combination of passages for cerclage cable (e.g., cerclage cable 104 on FIGS. 1A and 1B). Cerclage cable (e.g., cerclage cable 104 on FIGS. 1A and 1B) may be passed through a plurality of apertures 906 and cable button cavity 912. Hex cable button 900 may provide a plurality of passages for passing cerclage cable (e.g., cerclage cable 104 on FIGS. 1A and 1B) through hex cable button to provide a plurality of passage orientations relative to bone plate (e.g., bone plate 102 shown on FIGS. 1A and 1B). While not shown, hex cable button 900 may be threaded into bone plate aperture (e.g., bone plate aperture 1121 shown on FIGS. 1A and 1B). The angular orientation of hex cable button 900 may define the angular orientation of a cerclage cable (e.g., cerclage cable 104 on FIGS. 1A and 1B) passage. As hex cable button 900 is threaded onto bone plate (e.g., bone plate 102 shown on FIGS. 1A and 1B), annular orientation of hex cable button 900 may define angular orientation of the plurality of passages relative to bone plate (e.g., bone plate 102 shown on FIGS. 1A and 1B). Therefore, cerclage cable may secure bone plate (e.g., bone plate 102 shown on FIGS. 1A and 1B) to bone (e.g., bone 108 shown on FIG. 1A) in a plurality of potential positions.

Hex socket may cause hex cable button 900 to act similar to the head of a locking screw (not shown) for threading into bone plate aperture (e.g., bone plate aperture 112 on FIG. 1A). Hex opening 908 may provide driver access to hex socket 910. Furthermore, hex opening 908 may engage hex driver (not shown) to assist in screwing hex cable button 900 into or out of bone plate (e.g., bone plate 102 on FIGS. 1A and 1B).

Referring to FIG. 9D, first aperture 906*a* may intersect, i.e., provide fluid communication, with cavity 912. Cavity 912 may also be in communication with second and third apertures, 906*b* and 906*c*. The combination of first aperture 906*a* and second aperture 906*b* may provide a first cerclage cable passage (not shown). The combination of first aperture 906*a* and third aperture 906*c* may provide a second cerclage cable passage. Furthermore, the combination of second and third apertures, 906*b* and 906*c*, may provide a third cerclage cable passage.

Figure 10:
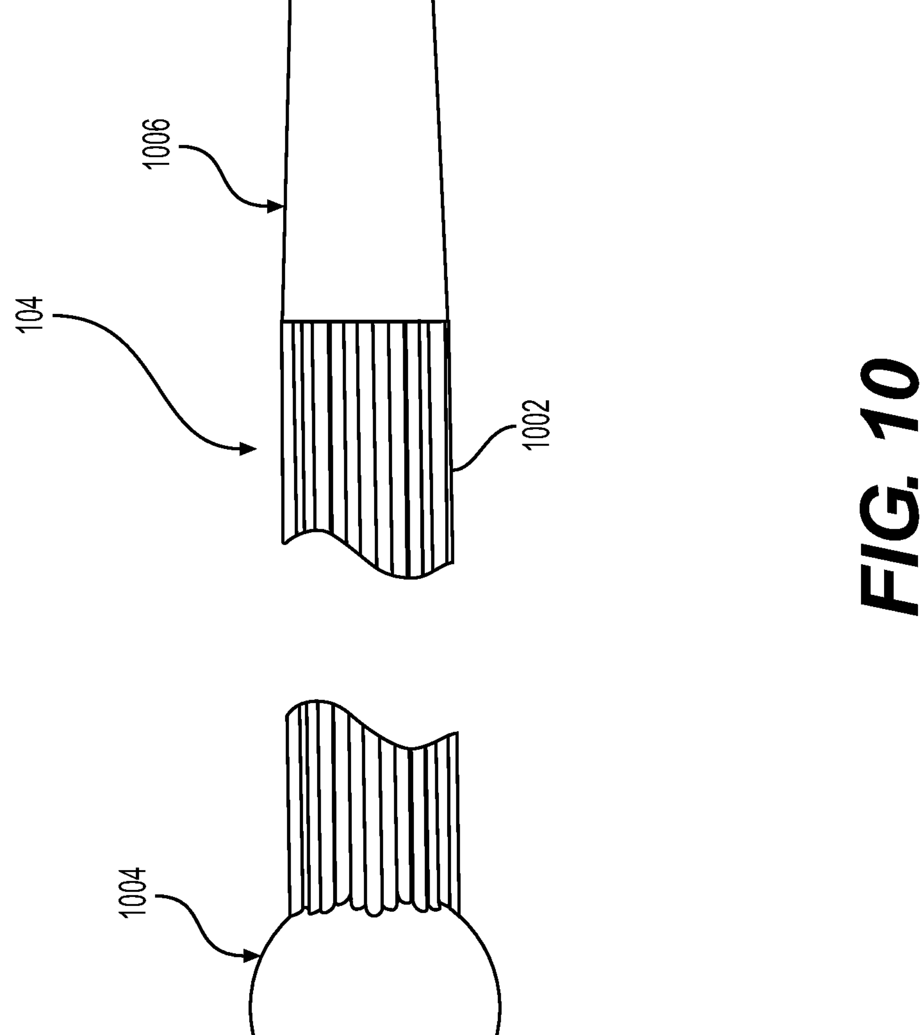
FIG. 10 illustrates a cerclage cable with exploded terminal ends, according to some embodiments.

FIG. 10 illustrates a cerclage cable 104, according to some embodiments, wherein cerclage cable's 1000 terminations are a bead 1004 on one end of strands 1002, and a swage 1006 on the other end.

Figures 11A, 11B, 11C:
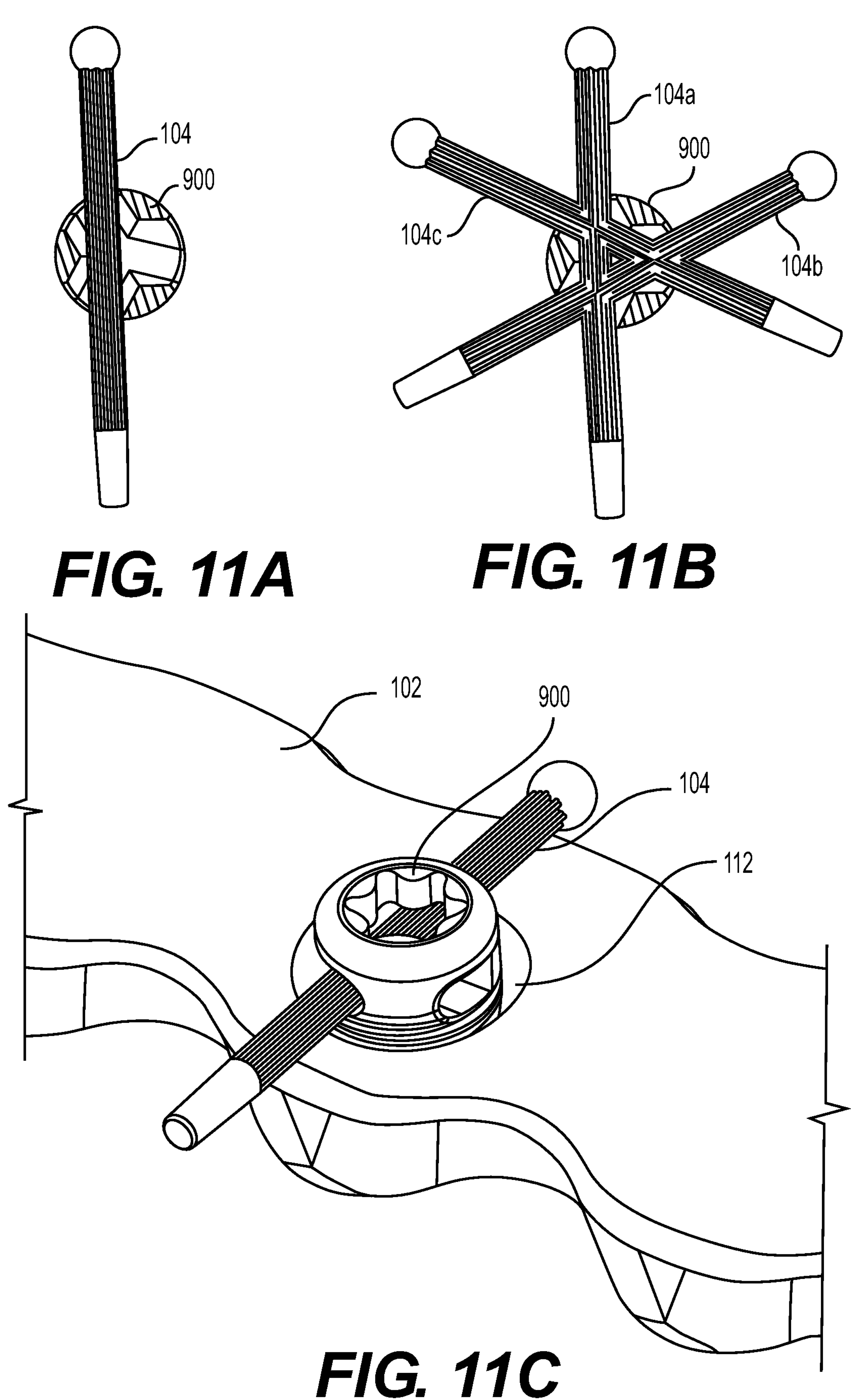
FIGS. 11A, 11B, and 11C illustrate cerclage cable routing options and cerclage cable combinations of a cerclage cable button with a hexalobular drive feature, including an illustration of a single routing option with a single cerclage cable, all three cable routing combinations superimposed, and the cerclage cable button and cerclage cable installed into a bone plate, respectively, according to some embodiments.

FIGS. 11A, 11B, and 11C illustrate cerclage cable 104 routing options and combinations of a hex cable button 900 with a hexalobular drive feature, including an illustration of a single routing option with a single cerclage cable 104, all three cable routing combinations superimposed, and the hex cable button 900 and cerclage cable 104 installed into a bone plate 102, respectively, according to some embodiments.

FIG. 11C illustrates hex cerclage cable button 900 installed onto bone plate 102 with cerclage cable 104 routed therethrough.

Figures 12A, 12B, 12C:
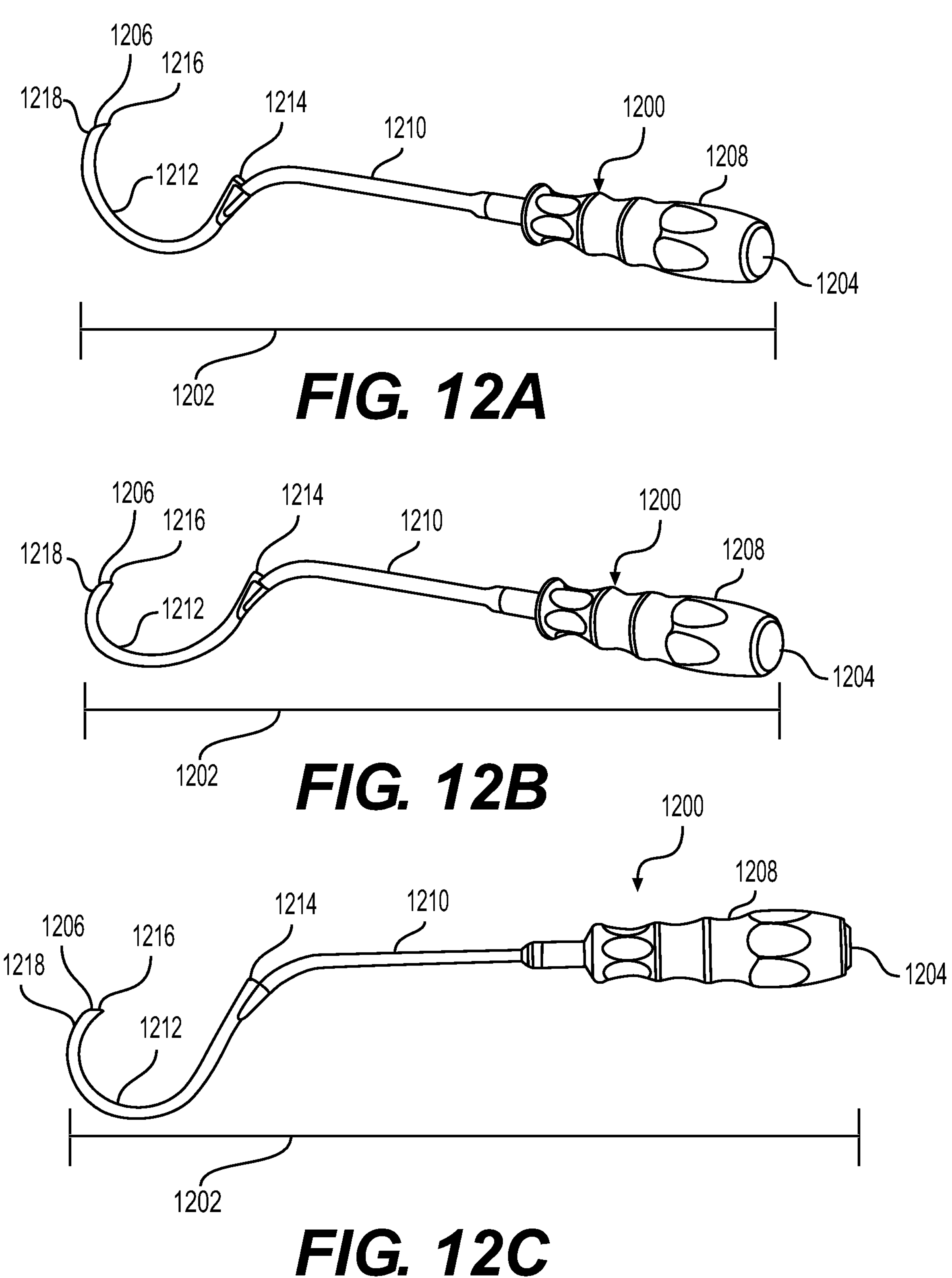
FIGS. 12A, 12B, and 12C illustrate embodiments of cable passers, including a straight cable passer, an offset cable passer, and a variable bend radius cable passer, respectively, according to some embodiments.

FIGS. 12A, 12B, and 12C illustrate a cable passer 1200, including a straight cable passer, an offset cable passer, and a variable bend radius cable passer, respectively, according to some embodiments. Cable passer 1200 may be comprised of a body 1202 comprising proximal end 1204 and distal end 1206. Handle 1208 may be disposed about proximal end 1204, wherein cable channel 1212 may be disposed about distal end 1206. Cable channel 1212 may be configured to receive a cerclage cable (e.g., cerclage cable 104 on FIGS. 1A and 1B). Cable channel entrance 1214 may be positioned on cable channel 1212 closest to proximal end 1204, whereas cable channel exit 1216 may be positioned at distal end 1206, wherein cable channel exit 1216 may comprise a cutting blade 1218 at distal end 1206. Detachable extension 1210 may be configured to be removably inserted into cable channel 1212 at or near cable channel exit 1214.

Figures 13A, 13B, 13C:
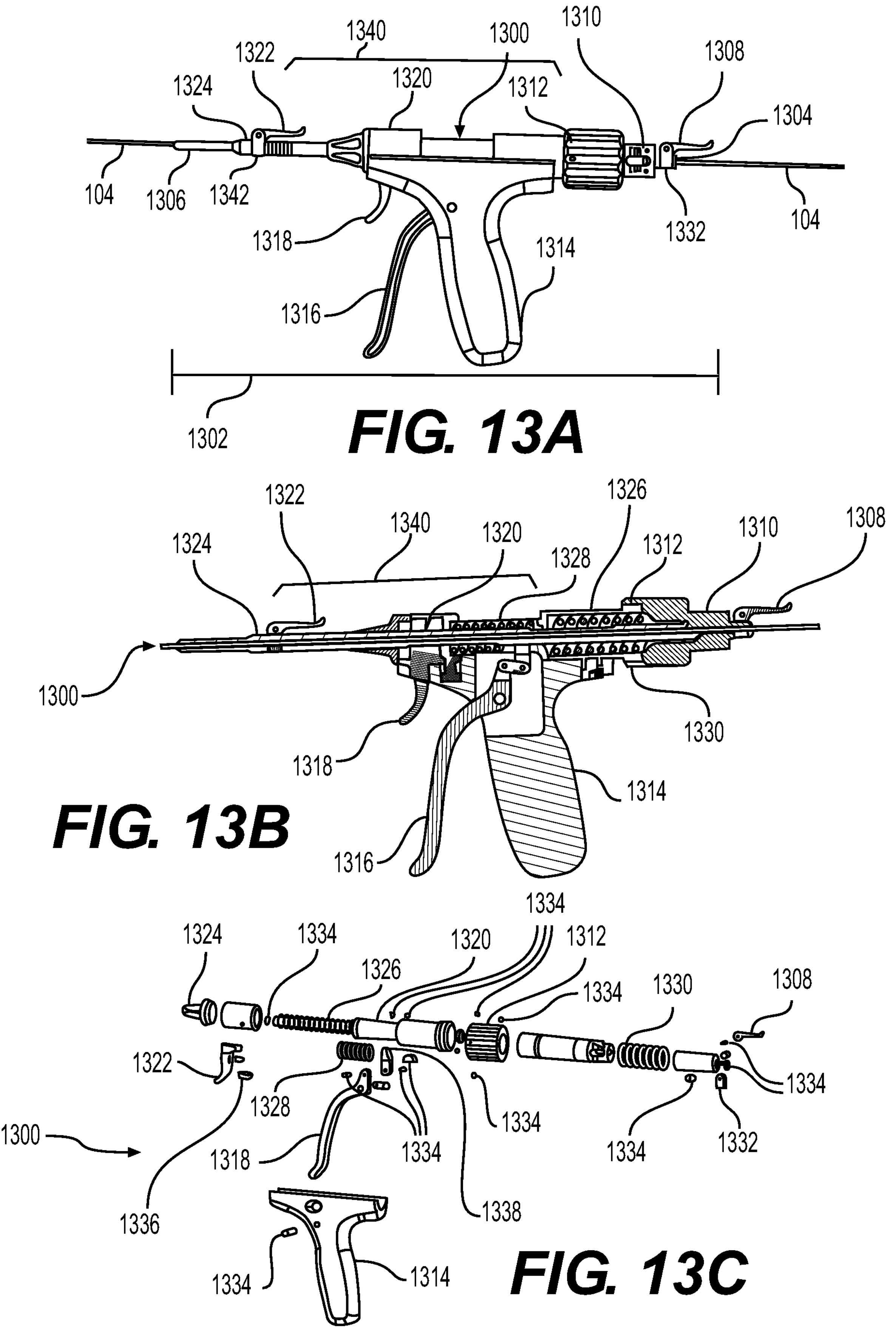
FIGS. 13A, 13B, and 13C illustrate a side view, a side isometric view and an exploded view, respectively, of a cerclage cable tensioner, according to some embodiments.

FIGS. 13A, 13B, and 13C illustrate a side view, a side isometric view and an exploded view, respectively, of cerclage cable tensioner 1300, according to some embodiments. Cerclage cable tensioner 1300 may comprise a body 1302 having a proximal end 1304 and distal end 1306, rear cam lock lever 1308, tension readout 1310, rotary actuator 1312, grip 1314, squeeze actuator 1316, tension release trigger 1318, shaft 1340, central shaft 1320, cam lock lever 1322, modular tip 1324, tension spring 1326, squeeze actuator 1328, and shaft return spring 1330.

Figure 14:
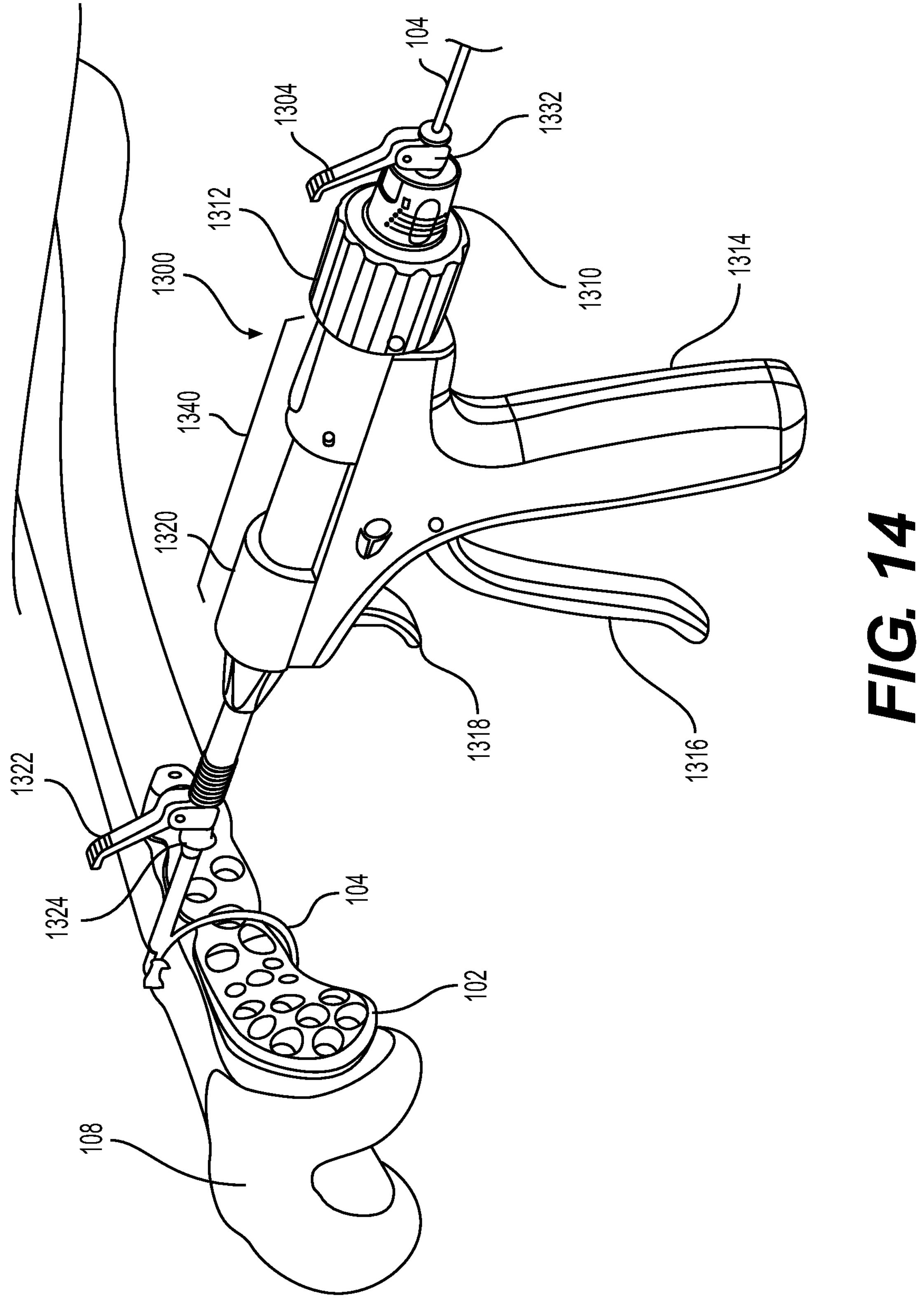
FIG. 14 illustrates a side perspective view of the positioning of a tensioner as a cerclage cable is passing through the tensioner, according to some embodiments.
Figures 15A, 15B:
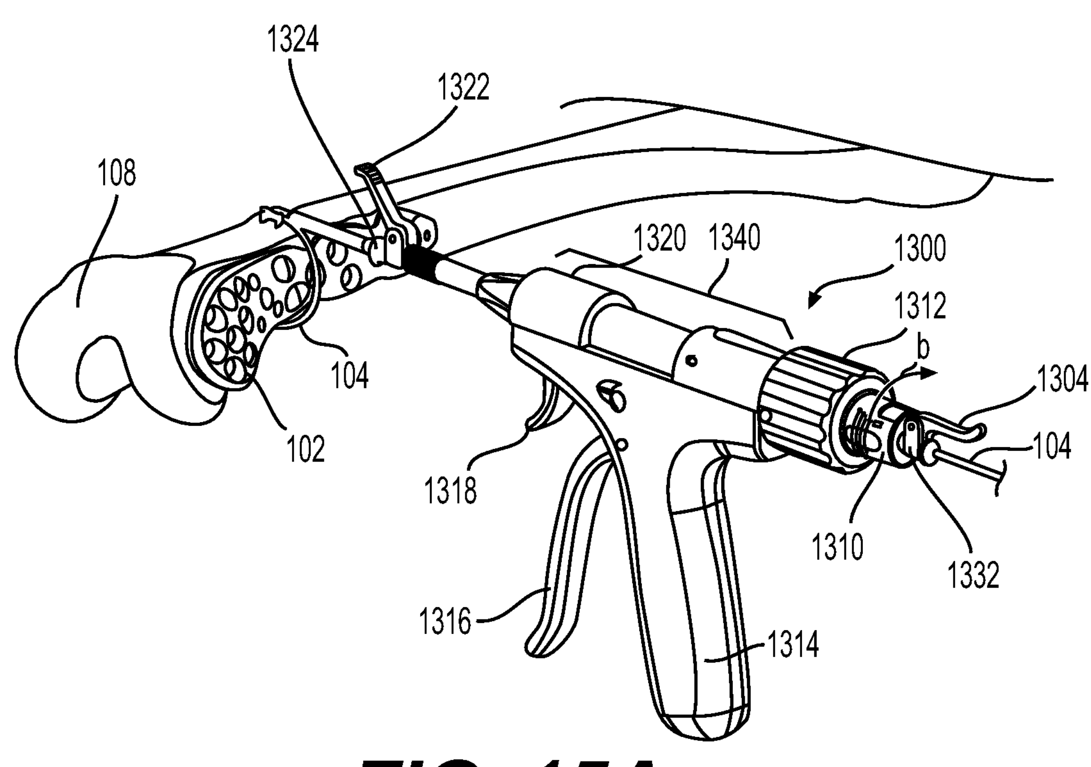
FIGS. 15A and 15B illustrate a side perspective view and a partial cross-sectional view, respectively, of a locked rear cam lock lever of a cerclage cable tensioner, according to some embodiments.
Figure 16A:
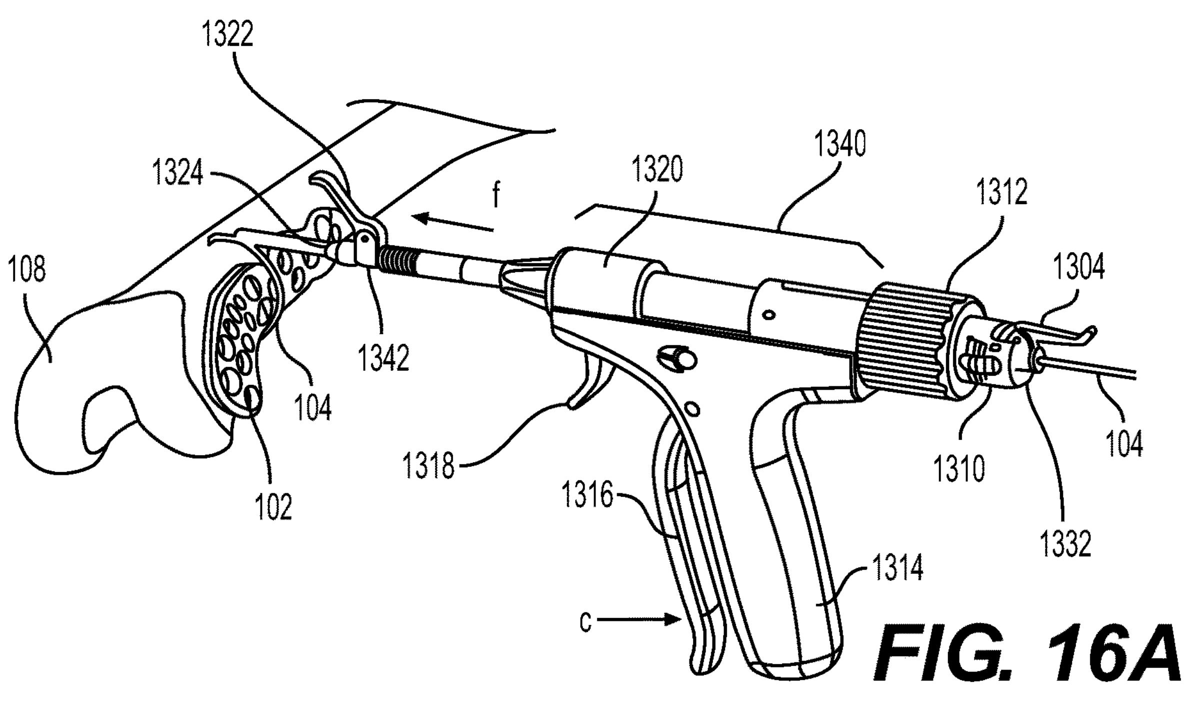
FIGS. 16A and 16B illustrate a side perspective view and a partial cross-sectional view, respectively of a squeeze actuator mechanism of a cerclage cable tensioner, according to some embodiments.
Figure 16B:
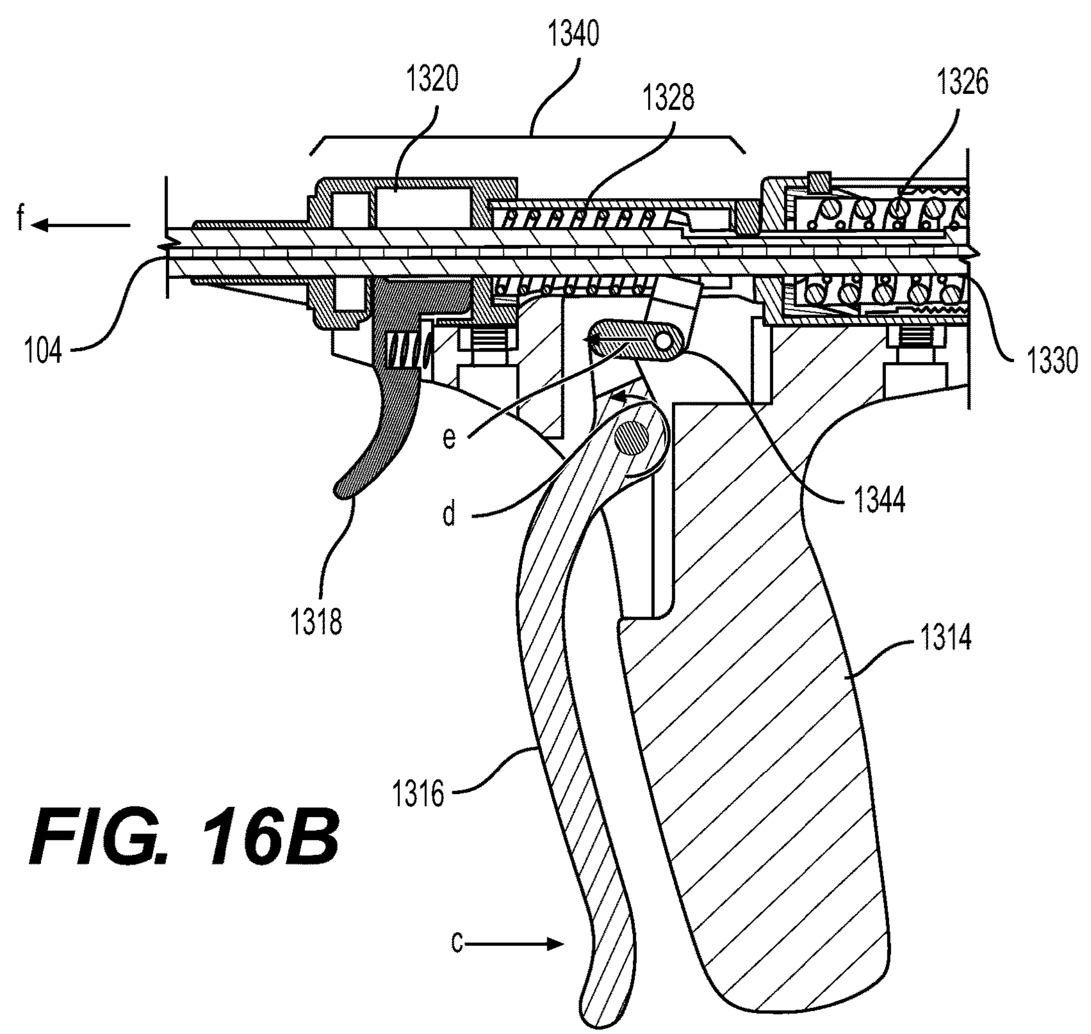
Figure 17A:
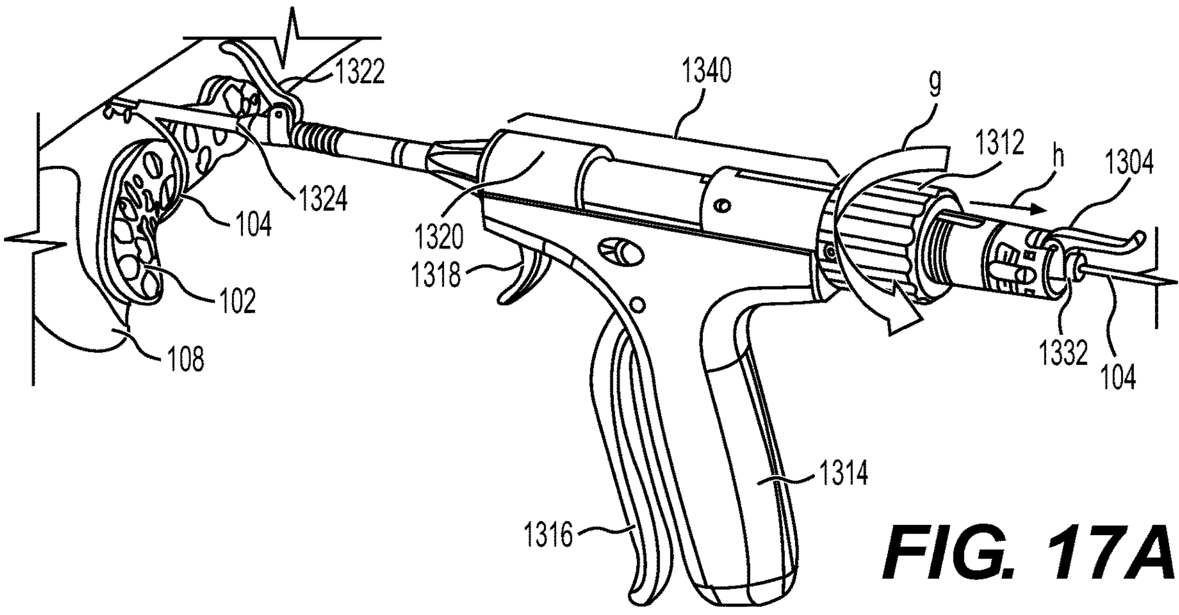
FIGS. 17A and 17B illustrate a side perspective view and a partial cross-sectional view, respectively of a rotary actuator mechanism of a cerclage cable tensioner, according to some embodiments.
Figure 17B:
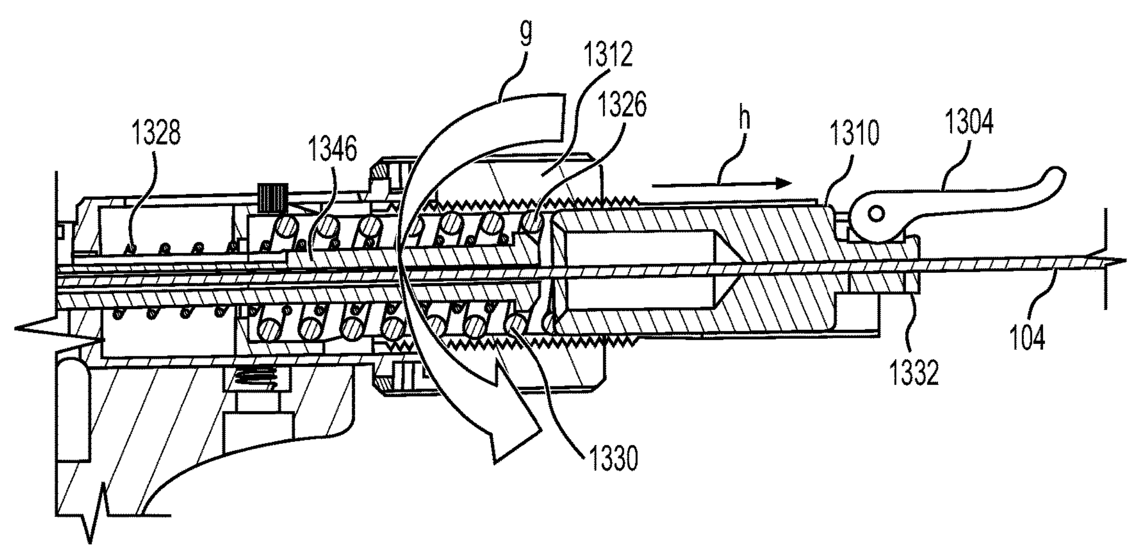
Figure 19A:
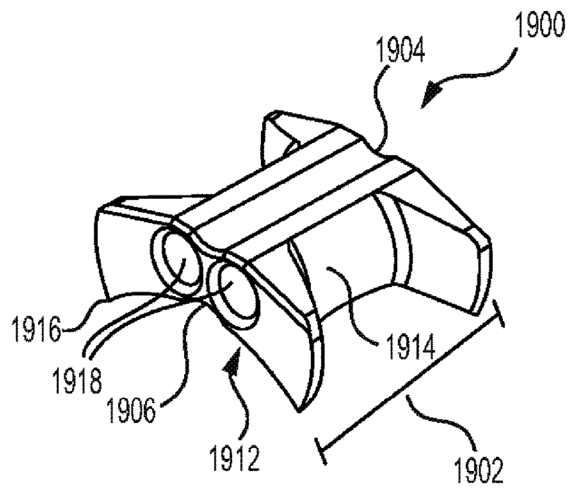
FIGS. 19A, 19B, 19C, and 19D illustrate an external side perspective view, an internal side plan view, a side view, and an internal isometric view, respectively of a crimp, according to some embodiments.
Figure 19B:
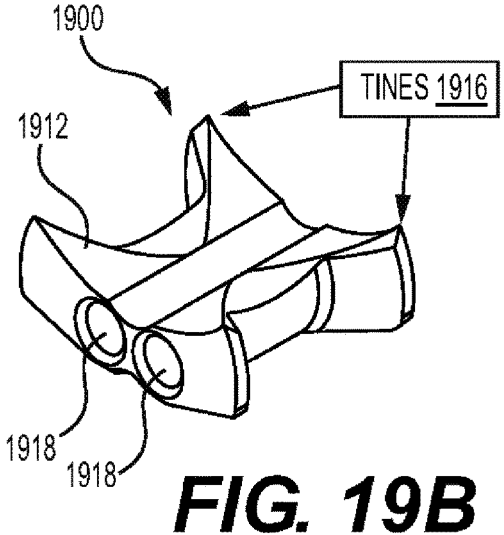
Figure 19C:
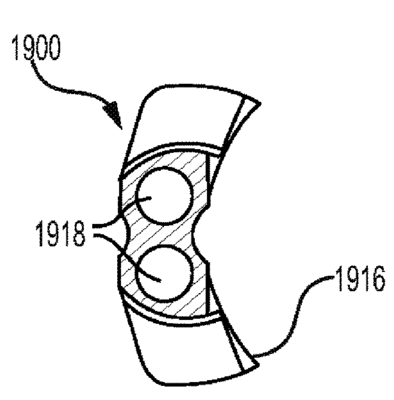
Figure 19D:
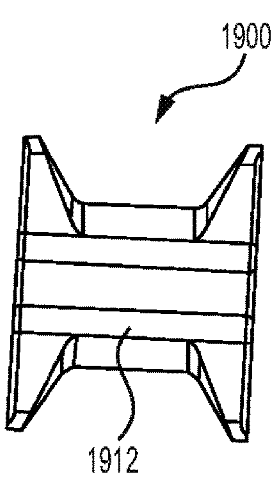

Referring to FIG. 14, modular tip 1324 may abut crimp 1900 Cerclage cable 104 may be passed through shaft 1340 and central shaft 1320, then pulled manually, exiting at proximal end 1304. Cerclage cable 104 may be pulled manually until there is no slack in cerclage cable 104. As shown in FIGS. 15A and 15B, rear cam lock 1332 may be engaged, as indicated by directional arrow a, by placing cam lock lever 1304 in a closed position, as indicated by directional arrow b. This action may secure cerclage cable 104 to cerclage cable tensioner 1300. As previously stated, the cerclage cable tensioner disclosed herein includes rotary actuated tensioning and squeeze actuated tensioning. Referring to FIGS. 16A and 16B, tension may be applied to cerclage cable 104 by depressing squeeze actuator 1316 as indicated by directional arrow c. As shown in FIG. 16B, squeeze actuator 1316 is connected to linkage 1344, which drives central shaft 1320 forward to apply tension to cerclage cable 104, as indicate by directional arrows c, d, e, and f. Referring to FIGS. 17A and 17B, tension force may be applied to cerclage cable 104 by rotating rotary actuator 1312 in one direction, as indicated by directional arrow g. When turned, rotary actuator 1312 may displace a threaded cylinder 1346, to apply tension to cerclage cable 1312. Referring to FIGS. 18A-18C, to release tension from squeeze actuator 1316, the user may pull trigger release 1318 to release a pawl (not shown) that may prevent central shaft 1320 from moving in one direction. Tension may be released by opening cam lock lever 1322, as indicated by direction arrow i, to allow cerclage cable 104 to move freely. Tension may also be released by opening rear cam lock lever 1304, as indicated by direction arrow j. Cerclage cable tensioner 1300 may comprise modular tip 1324 that may be used to lock cerclage cable 104 with provisional tension. Modular tip 1324, cam lock 1342, and cam lock lever 1322 may detach from cerclage cable tensioner 1300. Once the desired compression between bone plate 102 and bone 108 is achieved, crimp 1900 may be deformed by crimp tool (not shown) and modular tip 1324, cam lock 1342, and cam lock lever 1322 may be removed from cerclage cable 104.

FIGS. 19A, 19B, 19C, and 19D illustrate an external side perspective view, an internal side perspective view, a side view, and an internal isometric view, respectively of a crimp 1900, according to some embodiments. Crimp 1900 may comprise a body 1902 extending from a proximal end 1904 to a distal end 1906. The body 1902 may be sized and shaped to have a low-profile when positioned along a bone (not shown), including a first surface 1912 facing toward the bone and a second surface 1914 facing away from the bone (not shown).

The body may also comprise tines 1916, whereby tines may extend outward from a lateral surface thereof, which may extend between the first 1912 and second surfaces 1914. In some embodiments, the tines 1916 may be positioned at the distal end of the body. Some embodiments may comprise a pair of tines 1916, extending from opposing sides of the bone-abutting surface 1912. Some embodiments, as shown, may comprise two (2) pair of tines 1916.

Figure 20:
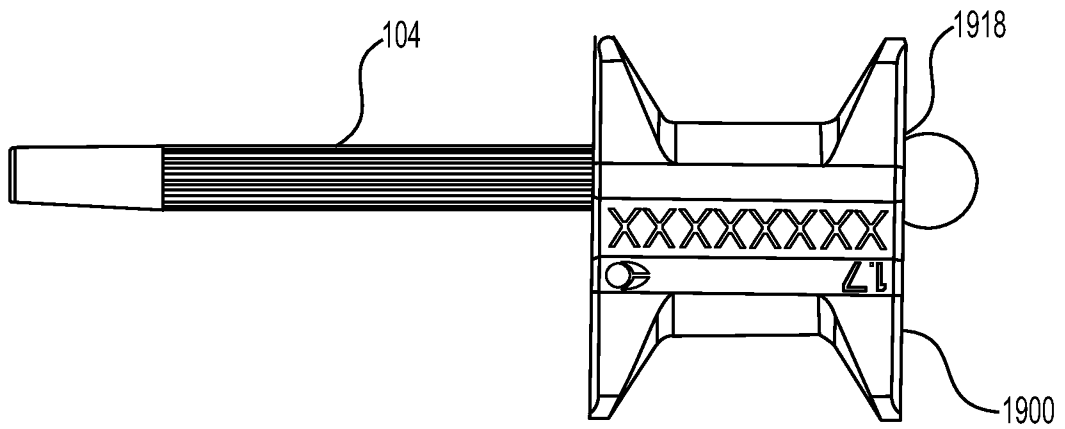
FIG. 20 illustrates a crimp positioned on a terminal end of a cerclage cable, according to some embodiments.

Crimp 1900 may further comprise lumens 1918 that may permit the entry of both terminal ends of a single cerclage cable 104. As depicted in FIG. 20, the lumens 1918 may be sized and shaped to permit the length of the cerclage cable 104 to be slid therethrough. Once the cerclage cable 104 has been looped around the bone 108, the cerclage cable 104 may be passed through the lumens 1918.

Figure 21A:
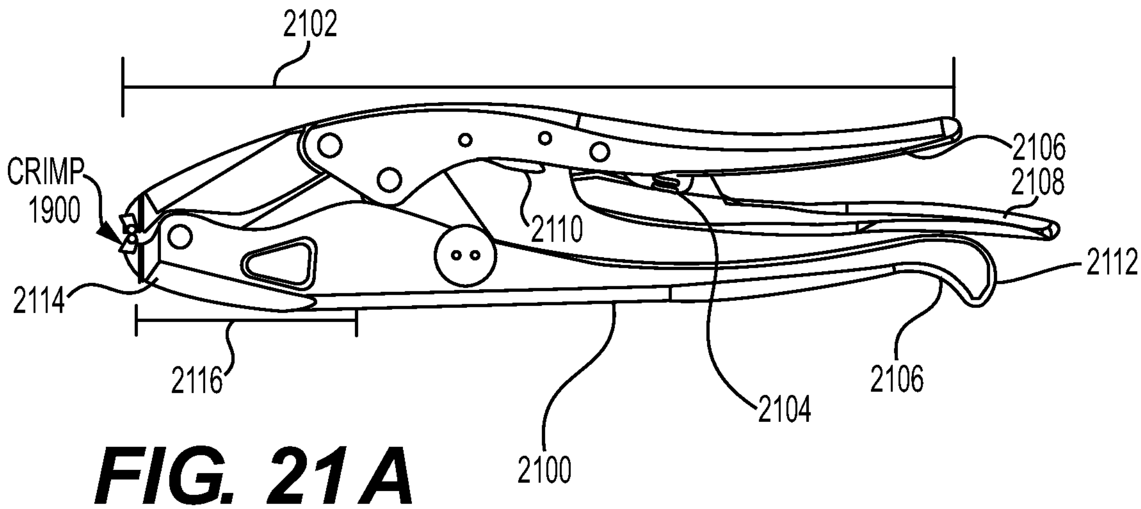
FIGS. 21A and 21B illustrate a side isometric view and a side plan view, respectively of a crimp tool, according to some embodiments.
Figure 21B:
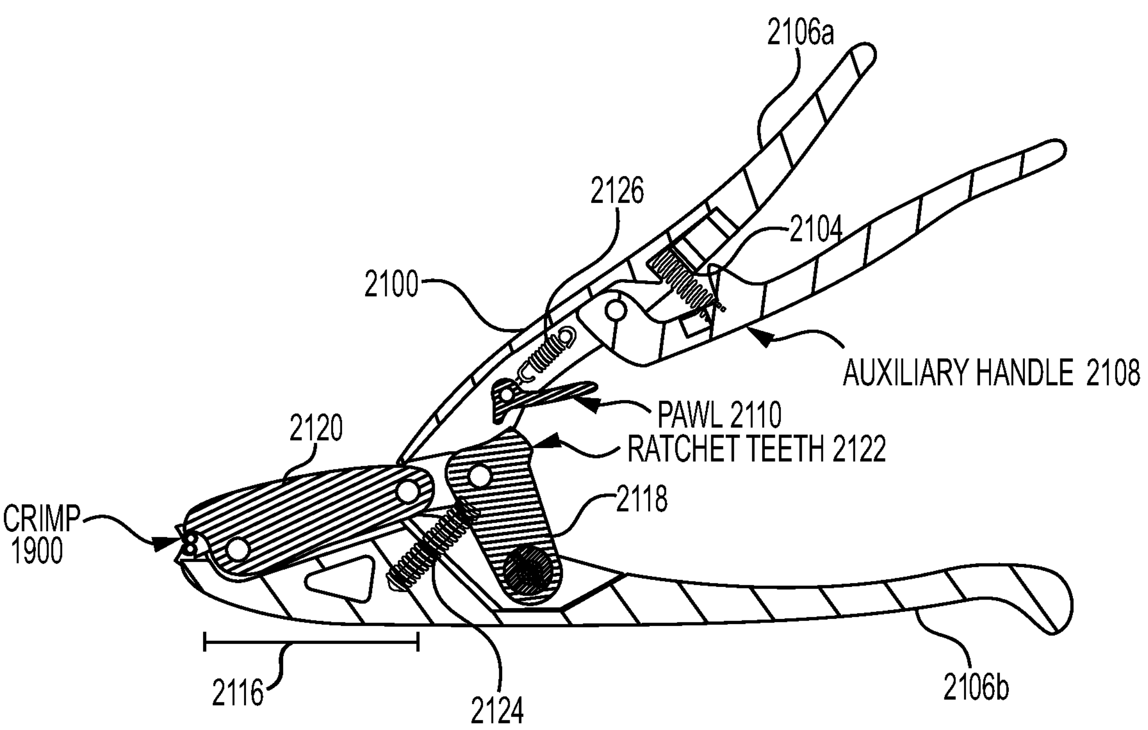

FIGS. 21A and 21B illustrate a side isometric view and a side perspective view, respectively of a crimp tool 2100, according to some embodiments. Crimping tool 2100 may be used to deform crimp 1900 (not shown). Crimp tool 2100 comprises body 2102 comprising proximate end 2112 and distal end 2114. Upper and lower handles 2106*a*, 2106*b* may open at proximate end 2112. Auxiliary handle 2108 may be coupled to upper handle 2106*a* toward proximate end 2112. Extended length nose 2116 may be disposed toward distal end 2114. The nose 2116 extends from a length of about 30 mm to about 60 mm. Pawl 2110 may be coupled to handle 2106*a* toward distal end 2114. Ratchet teeth 2122 may be coupled between upper handle 2106*a* and lower handle 2106*b*. Crimp tool 2100 may be used to deform crimp 1900 around cerclage cable 104 (not shown) and lock tension on the bone (not shown). Crimp tool further comprises a four-bar linkage (2118, 2120 shown) that may multiply the force applied at handles 2106*a*, 2106*b* and auxiliary handle 2108 to deform crimp 1900. Crimp tool 2100 further comprises auxiliary spring 2104, ratchet teeth spring 2124, and pawl spring 2126.

FIGS. 22A, 21B, and 22C illustrate a side view, a side plan view, and a cross-sectional view, respectively, of a flush cutter 2200, according to some embodiments. Flush cutter 2200 may comprise a body 2202 comprising a proximal end 2204 and a distal end 2206, and shaft 2216. Handle 2210 may be disposed at proximal end 2204, wherein actuator trigger 2212 may be moveably coupled to handle 2210. Modular blade cartridge 2208 may extend from shaft 2216 toward distal end 2206. Aperture 2218 may be disposed through modular blade cartridge 2208 at distal end 2206. Aperture 2218 may be sized to receive cerclage cable (not shown). Once cerclage cable (not shown) is passed through aperture 2218, modular blade cartridge 2208 may be positioned to abut against crimp (not shown). The user may squeeze trigger 2212, in the direction indicated by arrow k, wherein trigger 2212 may then actuate blade 2214, in the direction indicated by arrow 1, to cleanly shear excess cerclage cable (not shown).

Figure 23:
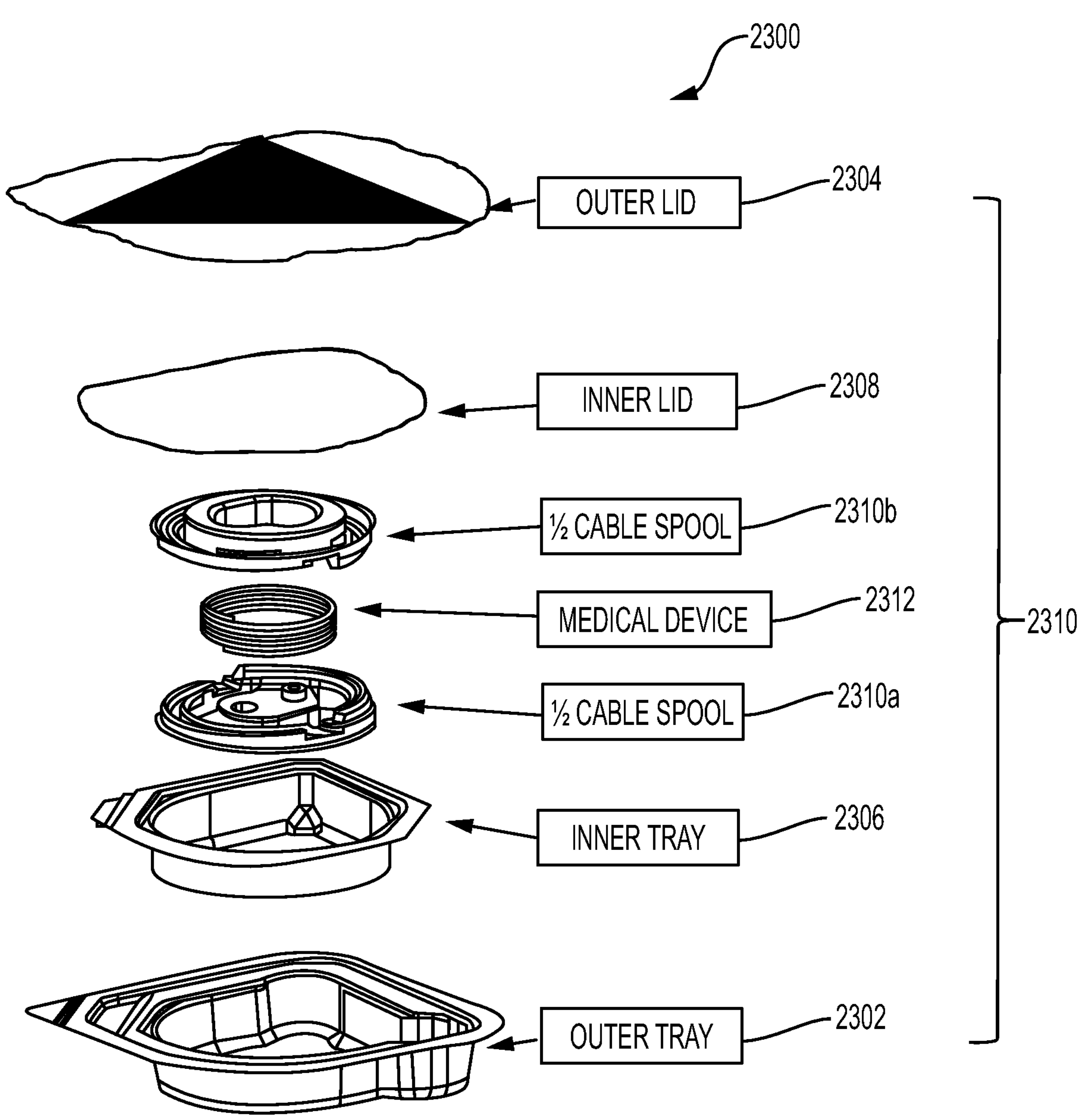
FIG. 23 illustrates a sterile packaging configuration for cerclage cables, according to some embodiments.

Sterile packaging for cerclage cables is also disclosed herein. Referring to FIG. 23, illustrating a configuration of sterile packaging 2300 for cerclage cables 2312, according to some embodiments. Sterile packaging 2300 comprises outer thermoformed plastic tray 2302 and outer lid 2304; inner thermoformed plastic tray 2306 and inner lid 2308; thermoformed plastic cable spool 2310, wherein cable spool 2310 may be comprised of a pair of identical half-spools 2310*a*, 2310*b*, wherein cerclage cables 2312 may be positioned inside of and dispensed from cable spool 2310.

Figure 24:
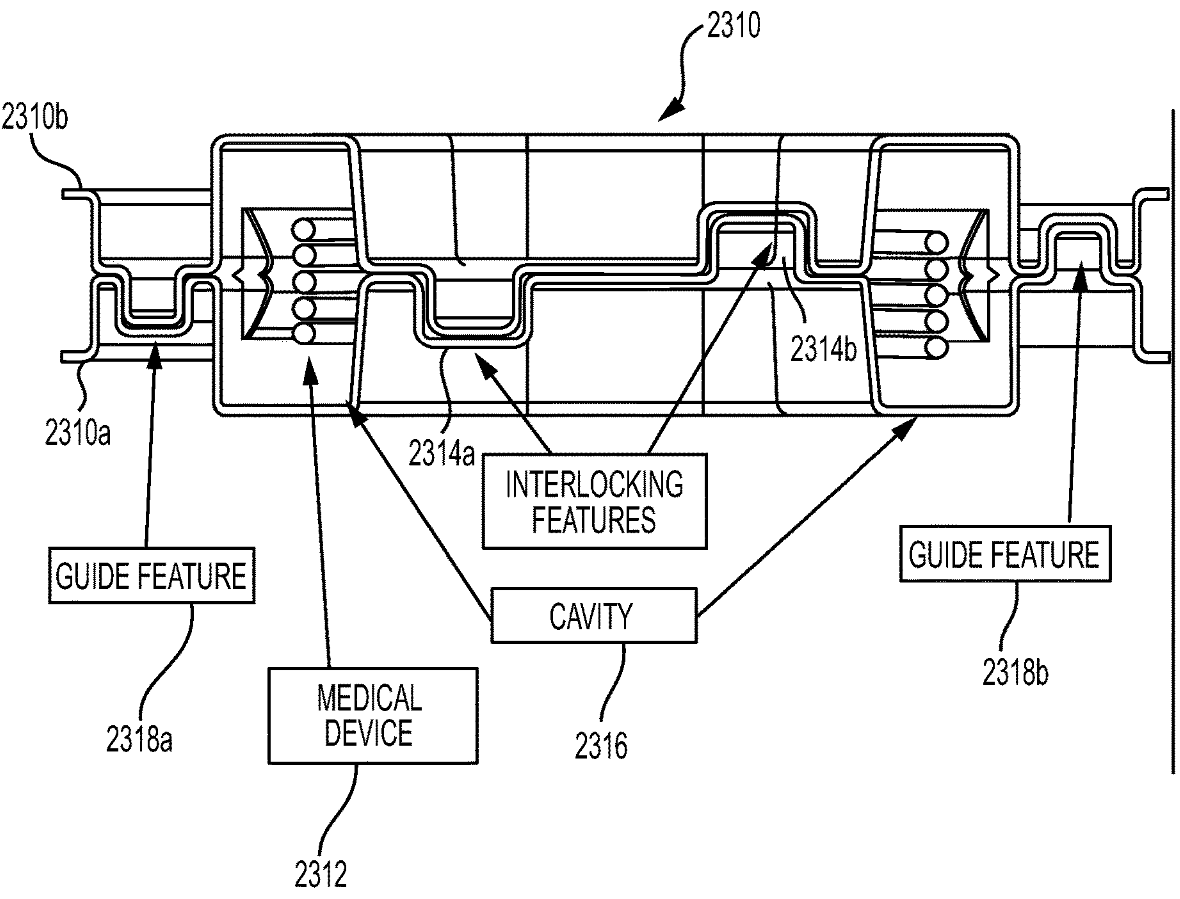
FIG. 24 illustrates an isometric view of a cable spool, according to some embodiments.
Figure 25:
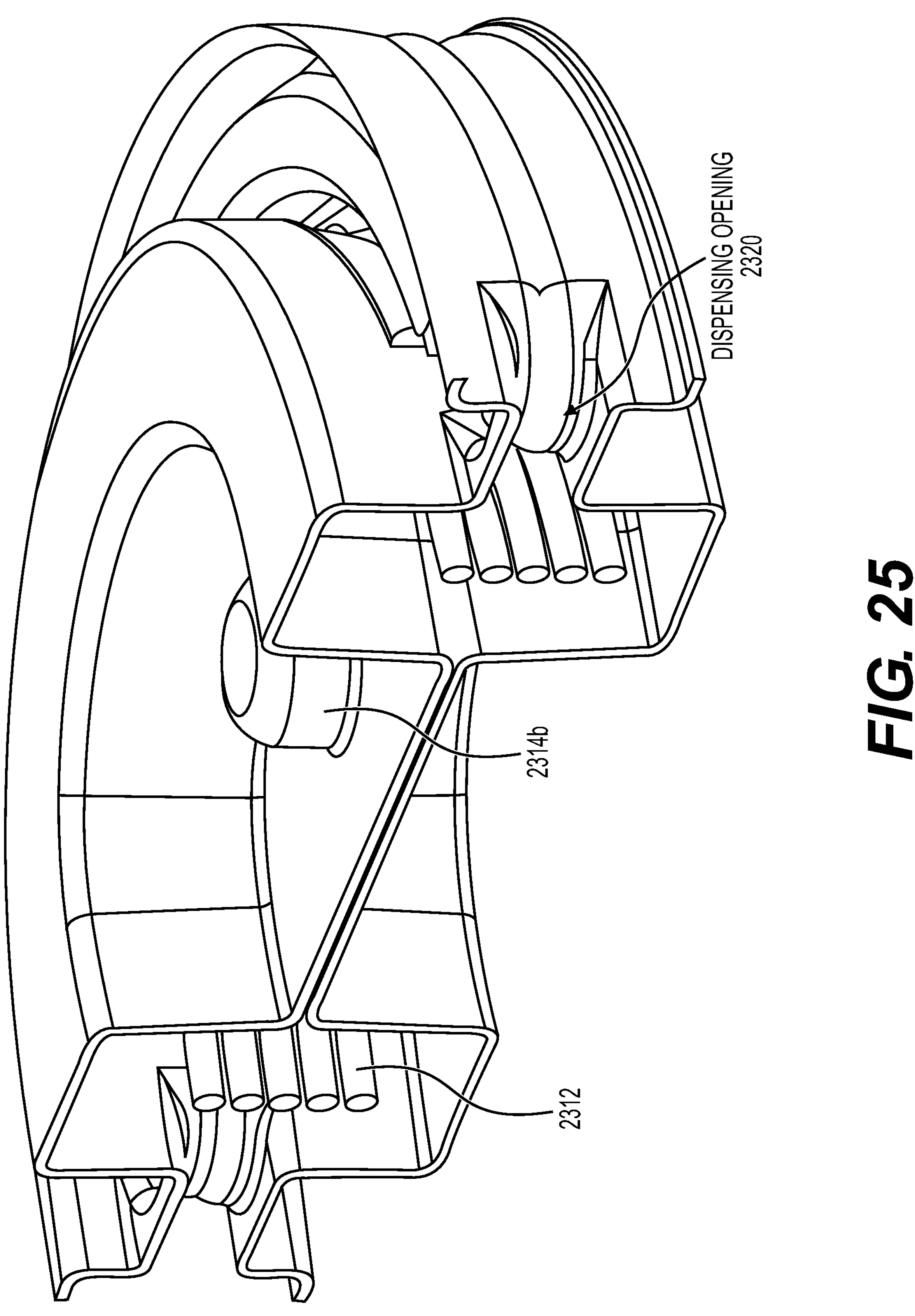
FIG. 25 illustrates a cross-sectional view of a cable spool, according to some embodiments.

Referring now to FIGS. 24 and 25. FIG. 24 illustrates a cross-sectional view of cable spool 2310, according to some embodiments. As shown, cable spool 2310 may include a pair of interlocking features 2314*a*, 2314*b* which connect to form cable spool 2310. Cable spool 2310 may also include a pair of guiding features 2318*a*, 2318*b* that maintain alignment of cerclage cables 2312. Once assembled the two half-spools 2310*a*, 2310*b* form a ring-like center cavity 2316 that house cerclage cables 2312. FIG. 25 illustrates a cross-sectional view of cable spool 2310, according to some embodiments.

FIG. 25 illustrates a cross-sectional view of a cable spool, according to some embodiments. Interlocking feature 2314, cavity 2316, cerclage cables 2312, and dispensing opening 2320, wherein cerclage cables 2312 may exit, are shown.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Various advantages of the present disclosure have been described herein, but embodiments may provide some, all, or none of such advantages, or may provide other advantages.

What is claimed is:

1. A method comprising:

passing a cerclage cable through a cerclage cable tensioner, wherein the cerclage cable tensioner comprises:

a body comprising a shaft having a proximal end and a distal end;

a modular tip disposed at the distal end of the shaft and removably affixed thereto;

a cam lock lever disposed proximally to the modular tip, wherein the cam lock lever controls the locking and unlocking of the cam lock, wherein the cam lock acts on the cerclage cable;

a manually rotatable rotary actuator threadably disposed toward the proximal end of the shaft, wherein the rotary actuator is manually rotatable in opposite directions by a user, wherein one direction displaces a threaded cylinder to apply tension to the cerclage cable, and wherein the opposite direction retracts the threaded cylinder, thereby decreasing tension to the cerclage cable;

a squeeze actuator coupled to a linkage, wherein the linkage drives a central shaft forward to apply tension to the cerclage cable, such that both the manually rotatable rotary actuator and the squeeze actuator are configured to apply tension to the cerclage cable;

a tension release trigger, wherein tension release trigger releases a pawl that prevents the central shaft from moving in one direction and thereby releases tension from the squeeze actuator;

a rear cam lock disposed at the proximal end of the shaft, wherein the rear cam lock secures the cerclage cable in the cerclage cable tensioner; and a rear cam lock lever, wherein the rear cam lock lever controls the locking and unlocking of the rear cam lock, locking the rear cam lock lever to secure the cerclage cable to the cerclage cable tensioner;

applying tension to the cerclage cable with the squeeze actuator, the rotary actuator, or combinations thereof;

locking the modular tip cam lock lever;

unlocking the rear cam lock lever;

detaching the modular tip, the cam lock, and the cam lock lever from the cerclage cable tensioner, wherein the modular tip, the cam lock, and the cam lock lever remain attached to the cerclage cable, and wherein a provisional tension on the cerclage cable is maintained; and removing the cerclage cable tensioner.

2. The method of claim 1, wherein the cerclage cable tensioner further comprises a handle grip disposed toward the proximate end of the shaft, wherein both the squeeze actuator and the tension release trigger extend therefrom and are coupled thereto.

3. The method of claim 1, further comprising wrapping the cerclage cable around a bone at least once before the step of passing the cerclage cable through the cerclage cable tensioner.

4. The method of claim 3, further comprising attaching a crimp to the cerclage cable after wrapping the cerclage cable around the bone at least once.

5. The method of claim 4, wherein the modular tip abuts against the crimp.

6. The method of claim 4, further comprising crimping or deforming the crimp before detaching the modular tip, the cam lock, and the cam lock lever from the cerclage cable.

7. The method of claim 6, further comprising cutting and removing excess cerclage cable extending from the crimp.

8. A method comprising:

passing a cerclage cable through a cerclage cable tensioner, wherein the cerclage cable tensioner comprises:

a body comprising a shaft having a proximal end and a distal end;

a modular tip disposed at the distal end of the shaft and removably affixed thereto;

a cam lock lever disposed proximally to the modular tip, wherein the cam lock lever controls the locking and unlocking of the cam lock, wherein the cam lock acts on the cerclage cable;

a manually rotatable rotary actuator threadably disposed toward the proximal end of the shaft, wherein the rotary actuator is manually rotatable in opposite directions by a user;

a squeeze actuator coupled to a linkage, wherein the linkage drives a central shaft forward to apply tension to the cerclage cable, such that both the manually rotatable rotary actuator and the squeeze actuator are configured to apply tension to the cerclage cable;

a tension release trigger, wherein tension release trigger releases a pawl that prevents the central shaft from moving in one direction and thereby releases tension from the squeeze actuator;

a rear cam lock disposed at the proximal end of the shaft, wherein the rear cam lock secures the cerclage cable in the cerclage cable tensioner; and a rear cam lock lever, wherein the rear cam lock lever controls the locking and unlocking of the rear cam lock, locking the rear cam lock lever to secure the cerclage cable to the cerclage cable tensioner;

applying tension to the cerclage cable with the squeeze actuator, the rotary actuator, or combinations thereof;

locking the modular tip cam lock lever;

unlocking the rear cam lock lever;

detaching the modular tip, the cam lock, and the cam lock lever from the cerclage cable tensioner, wherein the modular tip, the cam lock, and the cam lock lever remain attached to the cerclage cable, and wherein a provisional tension on the cerclage cable is maintained; and removing the cerclage cable tensioner.

9. The method of claim 8, wherein the cerclage cable tensioner further comprises a handle grip disposed toward the proximate end of the shaft, wherein both the squeeze actuator and the tension release trigger extend therefrom and are coupled thereto.

10. The method of claim 8, further comprising wrapping the cerclage cable around a bone at least once before the step of passing the cerclage cable through the cerclage cable tensioner.

11. The method of claim 10, further comprising attaching a crimp to the cerclage cable after wrapping the cerclage cable around the bone at least once.

12. The method of claim 11, wherein the modular tip abuts against the crimp.

13. The method of claim 11, further comprising crimping or deforming the crimp before detaching the modular tip, the cam lock, and the cam lock lever from the cerclage cable.

14. The method of claim 13, further comprising cutting and removing excess cerclage cable extending from the crimp.

* * * * *